United States Patent [19]

Hart

[11] Patent Number: 5,094,941
[45] Date of Patent: Mar. 10, 1992

[54] MONOCLONAL ANTIBODIES TO PDGF

[75] Inventor: Charles E. Hart, Brier, Wash.

[73] Assignee: ZymoGenetics, Inc., Seattle, Wash.

[21] Appl. No.: 139,960

[22] Filed: Dec. 31, 1987

[51] Int. Cl.$^5$ .................... C07K 15/28; G12N 5/20; G01N 33/577

[52] U.S. Cl. .................... 435/7.9; 435/7.94; 435/172.2; 435/240.27; 435/948; 435/975; 436/548; 436/808; 436/824; 530/388.24; 530/391.3; 530/413; 530/809; 935/104; 935/108; 935/110

[58] Field of Search .............. 435/172.2, 240.27, 810, 435/948, 7, 7.9, 975; 436/548, 808, 817, 824; 530/387, 391, 413, 808, 809; 935/104, 108, 110

[56] References Cited

U.S. PATENT DOCUMENTS

| | | | |
|---|---|---|---|
| 4,376,110 | 3/1983 | David et al. | 935/110 |
| 4,415,665 | 11/1983 | Mosbach et al. | 435/179 |
| 4,479,896 | 10/1984 | Antoniades | 530/399 |
| 4,689,220 | 8/1987 | Stermer et al. | 424/85.8 |
| 4,766,073 | 8/1988 | Murray et al. | 435/68 |
| 4,769,328 | 9/1988 | Murray et al. | 435/69.1 |
| 4,801,542 | 1/1989 | Murray et al. | 435/172.3 |
| 4,845,075 | 7/1989 | Murray et al. | 530/350 |
| 4,849,407 | 7/1989 | Murray et al. | 530/350 |

FOREIGN PATENT DOCUMENTS 8102899 10/1981 Int'l Pat. Institute .
WO85/00807 2/1985 PCT Int'l Appl. .

OTHER PUBLICATIONS

Kelly et al., Embo Journal, 4, 3399–3405, 1985.
Niman, Nature, 307, 180–183, 1984.
Betsholtz, C. et al., Nature 320:695–699 (1986).
Tong, B. D. et al., Nature 328:619–621 (1987).
Robson, B. et al., Int. J. Peptide Protein Res. 25:1–8 (1985).
Knudsen, K. A., Anal. Biochem. 147:285–288 (1985).
Clarke, L. et al., Meth. in Enzymol. 68:436–442 (1979).
Brown, J. P. et al., J. Biol. Chem. 255:4980–4983 (1980).
Alber, T. and Kawasaki, G., J. Mol. and Appl. Genet. 1:419–434 (1982).
Kurjan, J. and Herskowitz, I., Cell 30:933–943 (1982).
Beggs, J. D., Nature 275:104–108 (1978).
Köhler, G. and Milstein, C., Nature 256:495–497 (1975).
Köhler, G. and Milstein, C., Eur. J. Immunol. 6:511–519 (1976).
Waterfield et al., Nature 304:35–39, 1983.
Raines and Ross, J. Bio. Chem. 257:5154–5159, 1982.
Deuel et al., J. Bio. Chem. 256:8896–8899, 1981.
Antoniades, Proc. Natl. Acad. Sci. U.S.A. 78:7314–7317, 1981.
Johnsson et al., Biochem. and Biophys. Research Comm. 104:66–74, 1982.

Primary Examiner—David Saunders
Attorney, Agent, or Firm—Seed and Berry

[57] ABSTRACT

Monoclonal antibodies (MAbs) capable of binding to native PDGF, and MAbs capable of specifically binding to the PDGF-AA, PDGF-BB and PDGF-AB isoforms are disclosed. The subject MAbs may be used in the detection or purification of native PDGF or selected PGDF isoforms. In addition, the MAbs may be labeled with an imaging agent and used for in vivo diagnostic purposes, or combined with a pharmaceutically acceptable carrier or diluent for use within wound healing compositions.

50 Claims, 9 Drawing Sheets

MONOCLONAL ANTIBODIES TO PDGF

TECHNICAL FIELD

The present invention relates generally to the production of monoclonal antibodies, and more particularly, to the production and characterization of monoclonal antibodies capable of binding to native PDGF, as well as specifically binding to various PDGF isoforms.

BACKGROUND ART

Platelet-derived growth factor (PDGF) has been identified as one of the principal mitogens for many types of mesenchymal-derived cells grown in culture (reviewed by Ross et al. *Cell* 46:155-169, 1986). Due to both its ubiquitous distribution within the body and its chemotactic and mitogenic activities, PDGF has been proposed to play a role in a wide variety of multicellular responses, including wound healing, atherosclerosis, growth and development and neoplasia (Ross et al., ibid , 1986).

PDGF was first identified (Ross et al., *Proc. Nat'l. Acad. Sci. USA* 71:1207-1210, 1974; Kohler and Lipton, *Exp. Cell Res.* 87:297-30, 1974) and purified (Antoniades, *Proc. Nat'l. Acad. Sci. USA* 78:7314-7317, 1981; Deuel et al., *J. Biol. Chem.* 256:8896-8899, 1981; Heldin et al., *Biochemistry J.* 193:907-913, 1981; Raines and Ross, *J. Biol. Chem.* 257:5154-5160, 1982) from human platelets, where it is sequestered in the alpha granules and released upon platelet activation. It has subsequently been isolated from a variety of cell types (for review see Ross et al., ibid , 1986). These cell types include endothelial cells, vascular smooth muscle cells, monocytes and macrophages, derma fibroblasts, several tumor cell lies and a variety of virally transformed cell lines. Platelets have remained a major source of PDGF because outdated platelet material available through blood banks provides a large source of starting material. With the advent of recombinant DNA technology, PDGF has now been expressed in yeast cells (Murray and Kelly, EP 177,957, 1986), thus providing a non-mammalian source of material for therapeutic use.

PDGF is a cationic glycoprotein of approximately 31 kDa which exists as a disulfide-bonded, two-chain molecule. The protein exhibits size heterogeneity, with multiple species ranging from 27 to 31 kDa being observed (Raines and Ross, ibid., 1982). Upon reduction of the molecule, multiple protein species of 14 to 18 kDa are generated (Raines and Ross, ibid., 1982; Kaplan et al., *Blood* 53:1043-1052, 1979). These reduced species lack the biological activity of the native protein (Raines and Ross, ibid., 1982).

Amino acid sequence analysis of purified PDGF has revealed sequences for two distinct polypeptides, termed A-chain and B-chain, which have been reported to be present in equimolar amounts (Antoniades and Hunkapiller, *Science* 220:963-965, 1983; Waterfield et al., *Nature* 304:35-39, 1983; Doolittle et al., *Science* 221:275-277, 1983; Johnsson et al., *EMBO J.* 3:921-928, 1984). It is generally believed that the major form of PDGF in platelets is an A-B heterodimer (Johnsson et al., ibid. 1984). Naturally occuring A-chain homodimers and B-chain homodimers have been isolated from osteosarcoma cell-conditioned media (Heldin et al., *Nature* 319:511-514, 1986) and porcine platelets (Stroobant and Waterfield, *EMBO J.* 3:2963-2967, 1984), respectively. Kelly et al., (*EMBO J.* 4:3399-3405, 1985) have reported the production of mitogenically active recombinant B-chain homodimer using transformed yeast cells.

Amino acid sequence analysis of the A- and B-chains isolated from human platelets has shown them to be 54% homologous and to have lengths of 104 and 109 amino acids, respectively (Johnsson et al., ibid., 1984). The B-chain sequence has been shown to be highly homologous to the putative transforming protein (p28-sis) of the simian sarcoma virus (SSV) (Waterfield et al., ibid.; Doolittle et al., ibid.).

Both PDGF A-chain and B-chain cDNAs have recently been obtained (Betsholtz et al., *Nature* 320:695-699, 1986; Tong et al., *Nature* 328:619-621, 1987; Collins et al., *Nature* 328:621-624, 1987), including cDNAs encoding A-chain peptides of 110 and 125 amino acids.

In addition to its mitogenic and chemotactic activities, PDGF has been reported to trigger a wide variety of events following its binding to cell-surface receptors. At least two classes of PDGF receptors have been identified in our laboratory. These have been designated the "B-receptor," which binds only BB-homodimers (BB isoform), and the "A/B-receptor," which binds all three isoforms (AA-homodimers, BB-homodimers- and AB-heterodimers) of PDGF. The existence of such receptor classes may indicate differences in the biological events triggered by the different PDGF isoforms.

Various purification methods have been used to isolate PDGF. These methods generally involve numerous steps and are characterized by low overall yields of purified protein. Isolation of PDGF from human platelet lysates has been described by Heldin et al. (ibid., 1981). This method utilizes sequential chromatography on CM-Sephadex, Blue Sepharose, Bio-Gel P-150 and Sephadex G-200. This method, which provides an overall yield of 6%, was carried out on fresh platelets, a starting material which is not readily available. In another example, Johnsson et al. (*Biochem. Biophys. Res. Comm.* 104:66-74, 1982) used a series of three sequential chromatographies on CM-Sephadex, Blue Sepharose and Bio-Gel P-150 followed by high pressure liquid chromatography on a Lichrosorb RP 8 column to isolate PDGF derived from platelet lysates. Raines and Ross (ibid., 1982) reported a method to purify PDGF from outdated platelet-rich plasma which resulted in a maximum overall yield of 21%. In this method platelet lysates were subjected to four sequential chromatographies on CM-Sephadex, Sephacryl S-200, Heparin-Sepharose and Phenyl-Sepharose. Antoniades (U.S. Pat. No. 4,479,896, 1983) has reported a method for purifying PDGF from platelet lysates with a 1.5% yield. According to this method, platelet lysates are subjected to sequential precipitations with a primary fractionating reagent, comprising 1M NaCl and 1M acetic acid, and an alcoholic reagent, at a final volumetric concentration of 75%, to extract PDGF polypeptides. The partially purified PDGF polypeptides are then precipitated with acetone. The resultant precipitate is dissolved in chromatographic fluid and subjected to sequential chromatographies on CM-Sephadex, Bio-Gel P-150, and Blue Sepharose. These purification methods are complex and expensive, requiring extensive handling of samples resulting in large losses of material. These problems make the currently available purification methods unsuitable for commercial use.

The previously described methods also provide a PDGF protein product which is heterogeneous and of unknown dimer composition. Commercially available PDGF preparations are also of unknown composition. The dimer composition of the preparation may prove to be important in the therapeutic use of PDGF in view of the discovery of multiple PDGF receptors with different ligand binding specificities. None of the methods currently used to isolate PDGF provides separation of its isoforms (AA, BB and AB) from heterogeneous preparations while retaining the native conformation of the molecules. The only reported method for identification of A-chain and B-chain populations requires the purification of reduced forms of PDGF followed by HPLC analysis (Johnsson et al., ibid., 1982). This method does not lend itself to commercial application because renaturation of the reduced polypeptides does not restore native biological activity.

Previously described antibodies are unsuitable for isolation of specific PDGF isoforms. Available polyclonal antibodies against PDGF (Kelly et al., ibid.) do not demonstrate specificity for the individual isoforms. Monoclonal antibodies which recognize reduced forms of PDGF have been developed using a synthetic peptide derived from the amino-terminal amino acid sequence of the B-chain of PDGF as an immunogen (Niman et al., Proc. Nat'l. Acad. Sci. USA 82:7924–7928, 1985; Niman, Nature 307: 180-183, 1984). However, these antibodies detect the individual chains of PDGF only after reduction of the intact molecule an-d are therefore unsuitable for purifying or detecting the intact, active isoforms of PDGF.

In view of PDGF's clinical applicability in the treatment of injuries in which healing requires the proliferation of fibroblasts or smooth muscle cells and its further value as an important component of a defined medium for the growth of mammalian cells in culture, the production of useful quantities of PDGF is clearly invaluable. With the identification of two receptor classes for PDGF which have different ligand binding properties and with the potential that the individual isoforms of PDGF will stimulate biochemical events unique to each isoform, there is a clear need in the art for methods which allow the isolation of individual isoforms of PDGF in their native, active conformation. Present purification methods are complex and expensive, involving multiple manipulations of the starting material which result in substantial losses of active PDGF. The resultant PDGF product is heterogeneous in nature and contains unknown quantities of the various PDGF isoforms.

DISCLOSURE OF INVENTION

Briefly stated, the present invention discloses (1) monoclonal antibodies capable of binding to native PDGF, as well as specifically binding to the PDGF-AA, PDGF-BB and PDGF-AB isoforms; (2) immortalized cell lines that produce these monoclonal antibodies; and (3) methods for utilizing the monoclonal antibodies, for instance, in detecting the presence of or purifying native PDGF or various PDGF isoforms. In addition, the monoclonal antibodies of the present invention may be labeled with an imaging agent and used for in vivo diagnostic purposes.

As noted above, one aspect of the present invention provides a method for detecting the presence of native PDGF or various PDGF isoforms within biological samples. The method generally comprises (a) incubating monoclonal antibodies capable of binding to native PDGF or specifically binding to a selected PDGF isoform with the sample; and (b) detecting the presence of immune-complexes formed between the monoclonal antibodies and the biological sample, and therefrom determining the presence of native PDGF or the selected PDGF isoform. The method is applicable to detecting native PDGF or PDGF isoforms in a wide variety of biological samples, including plasma, whole blood, serum, platelet suspensions, cell-conditioned media, platelet or other cell lysates and fractionated cell culture media.

Another aspect of the present invention, as noted above, provides a method for purifying native PDGF or a selected PDGF isoform from a sample. The method generally comprises (a) immobilizing monoclonal antibodies capable of binding to native PDGF or specifically binding the desired PDGF isoform on a substrate; (b) contacting the sample with the immobilized antibodies under suitable conditions such that the antibodies bind to the native PDGF or the PDGF isoform; and eluting the native PDGF or PDGF isoform from the monoclonal antibody from the substrate.

In yet another aspect of the present invention, diagnostic kits incorporating the monoclonal antibodies described above in suitable containers are also disclosed. The respective monoclonal antibodies are immobilized within the container. The kits also include a labeled polyclonal antibody that is capable of binding to native PDGF or the selected PDGF isoform.

These and other aspects of the present invention will become evident upon reference to the following detailed description and attached drawings.

BEST MODE FOR CARRYING OUT THE INVENTION

Figure 1:
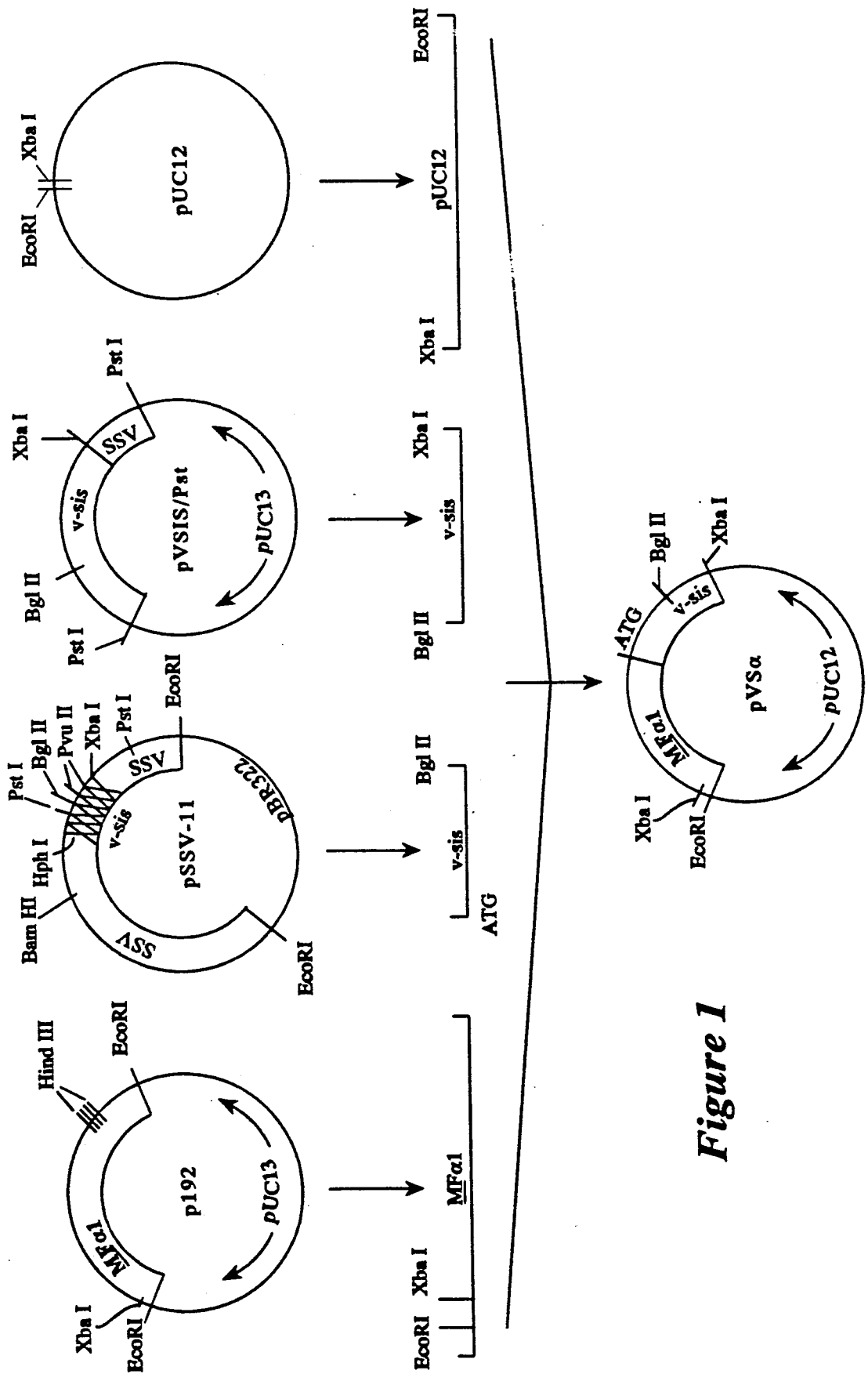
FIG. 1 illustrates the construction of a plasmid which contains the MFα1 promoter and secretory signal sequence upstream of the v-sis gene.

Prior to setting forth the invention, it may be helpful to an understanding thereof to set forth definitions of certain terms to be used hereinafter.

Native PDGF: Biologically active PDGF composed of two polypeptide chains joined by disulfide bonds (i.e. a dimer). Native PDGF exists in three forms: A chain homodimers, B-chain homodimers, and AB heterodimers. As used herein, the term "native PDGF" is applied to such molecules, individually or in combination, regardless of cell source. It can be obtained from, for example, platelets, tumor cell lines, or cells expressing cloned DNA sequences encoding the component polypeptides.

Isoform: The term isoform refers to one of the three potential dimeric compositions of PDGF. These are A-chain homodimers (AA), B-chain homodimers (BB) and AB heterodimers (AB).

Biological Sample: Any material derived from a living organism. A biological sample will generally contain cells, portions of cells or cell products, particularly proteins. Examples of biological samples include blood, urine, plasma, serum, platelet and other cell lysates, platelet releasates, cell suspensions, cell-conditioned culture media and chemically or physically separated portions thereof.

As noted above, PDGF has been shown to be a major mitogenic protein in the serum. Purified platelet PDGF has been shown to be a disulfide-bonded dimer. Studies of PDGF have shown that purified platelet PDGF contains two amino acid sequences, one A-chain and the other B-chain (Antoniades and Hunkapiller, ibid.; Waterfield et al., ibid.; Johnsson et al., ibid., 1984). Proposed structures of PDGF include AB-heterodimers, AA- and BB-homodimers. The existence of AA- and BB-homodimers in nature has been confirmed by the isolation of AA homodimers from an osteosarcoma cell line (Heldin et al., ibid., 1986) and BB-homodimers from porcine platelets (Stroobant and Waterfield, ibid.). Active PDGF B-chain homodimer analogs have also been expressed in yeast (Kelly et al., ibid.).

The present invention provides methods for purifying specific isoforms of PDGF from platelet lysates and other sources using monoclonal antibodies which bind to native PDGF and which specifically bind to one or more of the PDGF isoforms. These antibodies can also be used in a variety of assays for the detection of the individual isoforms of PDGF. As used herein, the term "specifically binds" is used to denote the recognition and binding of an antigen by an antibody. When applied to the interaction between an antibody and one or more isoforms of PDGF, "specifically binds" means that the antibody binds to the designated isoform(s) at a high level of affinity, while binding to other isoforms at less than 10% of that level. This difference in affinity can be seen as less than 10% cross-reactivity with other isoforms in an enzyme-linked immunosorbent assay (ELISA). In contrast to previously available antibodies, the specificity of the monoclonals provided by the present invention allows the isolation and purification of specific, active, non-reduced PDGF isoforms from native material. These isoforms may be used singly or in concert to provide a PDGF product of known composition and with full biological activity. The antibodies provide the additional advantage of allowing the recovery of up to 75% of the PDGF in the starting material.

According to the present invention, monoclonal antibodies are raised against specific isoforms or analogs of PDGF. These isoforms or analogs of PDGF may be purified from, for example, eucaryotic cells which naturally produce PDGF or they may be purified from eucaryotic cells which are expressing the protein from genetically manipulated DNA sequences. These DNA sequences will encode proteins having substantially the same biological activity as PDGF, and include the v-sis gene or derivatives of the v-sis gene, or portions thereof; DNA sequences encoding the human PDGF B-chain or portions thereof; DNA sequences encoding the human PDGF A-chain or portions thereof and DNA constructs containing both A- and B-chain sequences. Particularly preferred PDGF analogs and isoforms include PDGF B-chain homodimers and PDGF A-chain homodimers which can be produced in recombinant host cells as described in co-pending, commonly assigned U.S. patent applications Ser. Nos. 705,175 now abandoned and 896,485, now U.S. Pat. No. 4,766,073, respectively, which are incorporated by reference herein in their entirety. A particularly preferred source for these analogs or isoforms is yeast cells transformed with expression vectors comprising the DNA sequences encoding the appropriate PDGF isoforms or analogs, which express mitogenically active PDGF as described by Murray and Kelly (EP 177,957, 1986). AA- and BB-homodimers and AB-heterodimers may also be isolated from eucaryotic cells which naturally produce these molecules, particularly from cells which preferentially express one of the PDGF isoforms. For example, human AA-homodimers may be isolated from U2-OS osteosarcoma cell-conditioned media. Porcine BB-homodimers, which show some amino acid homology and common antigenic determinants with human B-chain, may be isolated from porcine platelets.

As noted above, a particularly preferred source of PDGF isoforms and analogs is a genetically engineered cell population which has been transfected or transformed with an expression vector comprising an appropriate DNA sequence encoding a PDGF isoform or analog ligated to an appropriate promoter. The use of genetically engineered cells permits the production of relatively large amounts of a single isoform. A preferred host cell is the yeast *Saccharomyces cerevisiae*. To facilitate protein processing and secretion the PDGF sequence is joined to a DNA sequence encoding a signal peptide recognized by the host cell. Methods of ligation of DNA fragments have been amply described (Maniatis et al., *Molecular Cloning: A Laboratory Manual*, Cold Spring Harbor Laboratory, N.Y., 1982) and are well within the skill of those of ordinary skill in the art to perform.

DNA sequences encoding proteins having substantially the same biological activity as PDGF may be isolated or constructed as has been described in the literature (Devare et al., *Proc. Nat'l. Acad. Sci. USA* 79:3179, 1982; Murray and Kelly, ibid.; Betshholtz et al., ibid.; Tong et al., ibid.; Collins et al., ibid.).

A sequence encoding PDGF B-chain may be constructed as described, for example, by Murray and Kelly ibid.). Briefly, the v-sis gene may be isolated from SSV-11 nonproductively infected normal rat kidney cells which have the SSV sequence integrated into their genome as described by Devare et al. (ibid.). The SSV DNA may be subcloned into an appropriate vector, for example, pBR322 (Bolivar et al., *Gene* 2:95-113, 1977). The amino terminal v-sis sequences which are not homologous to the sequence encoding human PDGF may be removed by in vitro mutagenesis. The 3' end of the v-sis sequence may be altered to remove the 3' non-coding region. This may be achieved by using an appropriate restriction endonuclease to remove a portion of the v-sis 3' coding sequence and replacing the 3' coding region with a synthetic double-stranded DNA fragment encoding the 3' terminus of the v-sis gene.

The human PDGF B-chain cDNA may be isolated from a human cDNA library made from an appropriate source of messenger RNA (mRNA) by using the v-sis gene or a fragment thereof as a hybridization probe, or through use of oligonucleotide probes designed from the B-chain DNA sequence. A preferred source of mRNA is human umbilical vein endothelial cells. These cells can be cultured in vitro for short periods of time and are known to secrete PDGF into the culture medium (DiCorleto and Bowen-Pope, *Proc. Nat'l. Acad.*

*Sci. USA* 80: 1919, 1983). The identity of this cDNA as that encoding PDGF may be verified by DNA sequencing. Alternatively, a human B-chain sequence may be constructed by mutagenesis of the v-sis gene.

The DNA sequence encoding the PDGF A-chain may be isolated from a human cDNA library made from an appropriate source of messenger RNA by using the v-sis gene or a fragment thereof as a hybridization probe or through the use of oligonucleotide probes designed on the basis of the A-chain DNA or amino acid sequences (Johnsson et al., ibid., 1984; Betsholtz et al., ibid., Tong et al., ibid.). Preferred sources of mRNA are human transformed cell lines, e.g., U2-OS and T-24. These cells can be cultured in vitro and are known to secrete a protein having PDGF-like activity (Heldin et al., ibid., 1986). The identity of this cDNA as that encoding A-chain may be verified by DNA sequencing. An alternate method of generating A-chain DNA sequence is described by Murray and Kelly (co-pending U.S. patent application Ser. No. 896,485 now U.S. Pat. No. 4,766,073). Briefly, the A-chain DNA sequence is synthesized using overlapping oligonucleotide duplexes. These oligonucleotide sequences are based on known A-chain amino acid sequence as determined by Johnsson et al. (ibid., 1984). Preferably, the sequence will be designed to reflect optimal codon usage for the particular host cell.

For expression, DNA sequences encoding PDGF isoforms and analogs are joined to a suitable promoter. Promoters which may be used in yeast include the ADH2 promoter (Young et al., in *Genetic Engineering of Microorganisms for Chemicals*, Hollaender et al., eds., p. 335, Plenum, NY, 1982), the ADH2-4c promoter (Russell et al., *Nature* 304:652–654, 1983), and the MFα1 promoter (Kurjan and Herskowitz, *Cell* 30:933–943, 1982). A particularly preferred promoter is the TPI1 promoter (Alber and Kawasaki, *J. Mol. Genet. Appl.* 1:419, 1982 and Kawasaki, U.S. Pat. No. 4,599,311).

The constructions described herein were designed such that the PDGF isoform or analog would be secreted from the yeast cell into the medium. This was accomplished through the use of a secretory peptide which directs the protein into the secretory pathway of the yeast cell. A preferred secretory peptide is the pre-pro signal peptide of the yeast mating pheromone alpha-factor (Kurjan and Herskowitz, ibid.; Julius et al., Cell 36:309, 1984; Brake et al., *Proc. Nat'l. Acad. Sci. USA* 81:4642, 1984; and Kurjan et al., U.S. Pat. No. 4,546,082), although other secretion signals may be used.

To ensure the efficient transcription, termination and polyadenylation of mRNA, a yeast terminator sequence was added. A preferred terminator is the TPI1 terminator (Alber and Kawasaki, ibid.).

Once appropriate PDGF expression units are constructed, the expression units are inserted into a yeast/*E. coli* shuttle vector. Suitable vectors include YEp13 (Broach et al., *Gene* 8:121–133, 1979), YRp7 (Stinchcomb et al., *Nature* 282:39–45, 1979), pJDB219 and pJDB248 (Beggs, *Nature* 275:104–108, 1978) and derivatives thereof. Such vectors may include any dominant marker for which a method of selection exists. Such selectable markers may include a nutritional marker, for example, LEU2, which allows selection in a host strain carrying a leu2 mutation, or a gene which encodes antibiotic resistance, for example, chloramphenicol transacetylase, which enables cells to grow in the presence of chloramphenicol. Alternatively, an "essential gene", for example the POT1 gene of *Schizosaccharomyces pombe*, which complements a tpi1 mutation in the host cell, allowing cells to grow in the presence of glucose, may be used as a selectable marker (Kawasaki and Bell, EP 171,142).

It is preferable to use a vector which is stably maintained within the host cell. A suitable yeast vector in this regard in the plasmid pMPOT2 (deposited with ATCC, accession number 20744), which includes the POT1 gene and the REP1, REP2, REP3 and ori of the 2 micron plasmid.

After preparation of the expression units, the constructs are transformed into suitable host cells. Techniques for transforming yeast are well known in the literature and have been described, for instance, by Beggs (ibid.) and Hinnen et al. (*Proc. Nat'l. Acad. Sci. USA* 75:1929–1933, 1978). Suitable yeast host strains may carry a genetic defect which is complemented by the selectable marker present on the yeast vector. Positive transformants are selected using the selectable marker present on the yeast vector. Yeast strains having such defects are widely available, such as from the American Type Culture Collection, Rockville, Md., or may be prepared using standard techniques of mutation and selection.

Expression of biologically active PDGF isoforms in eucaryotic cells other than yeast cells can be achieved by a person skilled in the art through use of appropriate expression/regulatory signals. Transcriptional promoters capable of directing the expression of these sequences are chosen for their ability to give efficient and/or regulated expression in the particular eucaryotic cell type. Signal sequences capable of directing the gene product into the cell's secretory pathway are chosen for their function in the appropriate cell type. Other useful regulatory signals, such as transcription termination signals, polyadenylation signals and transcriptional enhancer sequences, are also chosen for their function in the appropriate cell type, the selection of which would be apparent to an individual skilled in the art.

Proteins produced from the transformed or transfected cells may be purified by conventional methods. Useful isolation techniques include precipitation- and fractionation by a variety of chromatographic methods.

In a preferred purification procedure, concentrated yeast supernatant broth is chromatographed on an S-Sepharose Fast Flow column and eluted with a step gradient of sodium chloride. The resulting eluate is acidified and chromatographed on a second S-Sepharose column. PDGF is eluted from this column with a gradient of ammonium acetate. The eluate from this column is fractionated on a Sephadex G-50 Superfine column. Fractions are analyzed by electrophoresis on SDS-polyacrylamide gels and the purest fractions are pooled. Additional purification procedures are known in the art; see, for example, Heldin et al (ibid., 1981); Raines and Ross (ibid., 1982); and Antoniades (ibid., 1983).

PDGF isoforms and analogs are used to make monoclonal antibodies according to methods generally described in the literature. Preferred subject animals are mice or rats, with BALB/c mice being particularly preferred. The appropriate animals are immunized with a preparation of the PDGF isoform of interest, preferably a pure or partially pure preparation of a single isoform. Preferably, the animals are immunized with at least 100 ng each of the protein preparation, most preferably greater than 500 ng each. For immunization, the PDGF preparation is preferably adsorbed to a solid phase matrix, preferably to nitrocellulose paper. The paper is then introduced into the animal. Techniques for introduction of the adsorbed PDGF preparation include implantation (U.S. Pat. No. 4,689,220) or solubilization of the solid phase and injection of the solubilized material (Knudsen, *Anal. Biochem.* 147:285–288, 1985). The solid phase matrix may be solubilized in an appropriate organic solvent (e.g., DMSO) and either mixed with adjuvant or saline, or injected directly. Alternatively, the PDGF preparation may be injected in the absence of a solid matrix and/or adjuvant. Injection or implantation may be intraperitoneal, subcutaneous, intramuscular or intravenous, preferably intraperitoneal. The animals may also be injected with adjuvant, such as Freund's adjuvant. Single or multiple booster immunizations are used. Between one and seven days prior to the fusion date, preferably on days one through four, intravenous injections of the appropriate PDGF isoform or analog may be given daily.

Between one and seven days, preferably four days, after the administration of the final booster immunization, spleens or portions thereof are harvested from the immunized animals. At this time, the lymph nodes may also be harvested and included in the cell preparation. The harvested organs are minced using techniques which disrupt the structure of the organ, but which are not detrimental to the lymphocytes. The organs are preferably minced with scissors, pressed through a mesh screen and mixed with growth medium to enrich the preparation for lymphocytes. The minced and strained tissue is harvested by centrifugation, then mixed with growth medium to form a cell suspension. The red blood cells may be lysed by adding a hypotonic or hypertonic solution to the cell suspension. A preferred method for cell lysis is to add distilled water to the suspensions and quickly return the suspensions to an isotonic state with sodium chloride. Any remaining tissue may be removed by filtration through gauze.

The harvested cell suspension is then mixed with a myeloma cell line, preferably one which is syngeneic with the immunized animal. Myeloma cell lines from various species are widely available through, for example, American Type Culture Collection, Rockville, Md. Myeloma cell lines commonly used include P3X63Ag8 (ATCC TIB 9), SP2/0-Ag14 (ATCC CRL 1581), OF (ATCC CRL 1646) and 210-RCY-Agl (Galfre et al., *Nature* 277:131, 1979). A preferred cell line is P3/NS1/1-Ag4-1 hereinafter referred to as NS-1 (ATCC TIB 18). The NS-1 cells are preferably tested to determine the cloning efficiency of the strain. This may be done by cloning out the NS-1 strain by limiting dilution and carrying out test fusions with the individual NS-1 clones to find candidates with the highest fusion efficiencies. The myeloma cells are cultured in an appropriate mammalian cell growth medium, a variety of which are generally known in the art and available from commercial sources. Mammalian cell lines are routinely grown between 36° C. and 40° C. under conditions which maintain an optimal pH between 6.0 and 8.0, preferably about pH 7.2. pH may be maintained through the use of a variety of buffer systems known in the art. A preferred buffer system involves growing the cells in a bicarbonate buffer in a humidified incubator containing $CO_2$, preferably about 7% $CO_2$.

The fusion between the lymphocytes from the immunized animal and the myeloma cells may be carried out by a variety of methods described in the literature. These methods include the use of polyethylene glycol (PEG) (Brown et al., *J. Biol. Chem.* 255:4980–4983, 1980) and electrofusion (Zimmerman and Vienken, *J. Membrane Biol.* 67: 165–182, 1982; an electrofusion generator is commercially available from Biotechnologies and Experimental Research, Inc., San Diego, CA).

Following the fusion, the cells are plated into multi-well culture plates, preferably 96-well plates. A reagent which selectively allows for the growth of the fused myeloma cells over the unfused cells is added to the culture medium. A preferred selection technique uses HAT (hypoxanthine, aminopterin, thymidine) selection. Other selection techniques may also be used depending on the myeloma cell line used.

Alternative methods of producing monoclonal antibodies utilize in vitro immunization techniques. Lymphocytes may be harvested from lymphoid organs, such as spleen or lymph nodes, or from whole blood as peripheral blood lymphocytes. The lymphocytes are put into culture in the presence of the appropriate PDGF isoform or analog. Often immunostimulatory polypeptides will be added to the culture medium concurrently. At various times following the culturing of the lymphocytes in vitro, the lymphocytes are harvested and fused with a myeloma cell line as described above.

Other techniques for producing and maintaining antibody secreting lymphocyte cell lines in culture include viral transfection of the lymphocyte to produce a transformed cell line which will continue to grow in culture. Epstein bar virus (EBV) has been used for this technique. EBV transformed cells do not require fusion with a myeloma cell to allow continued growth in culture.

Thymocytes may be used as a feeder layer to condition the medium for the fused cells. Alternatively, peritoneal macrophages or non immune spleen cells may be used as a feeder layer. Another alternative is to use conditioned medium from thymocytes or macrophages. Thymocytes may be prepared from juvenile mice less than 8 weeks old. The thymus glands are harvested and minced using techniques which disrupt the thymus gland but are not detrimental to the thymocytes. This procedure is preferably carried out using scissors to mince the tissue, followed by passage of the tissue through a mesh screen. The minced and strained cell material is then harvested by centrifugation. Cell suspensions are made using growth medium. Any remaining connective tissue may be removed by filtration through gauze.

At an appropriate time following the fusion day, the fused cells (hybridomas) are then analyzed for the production of antibody against the antigen of choice. This can be done by a wide variety of techniques, including Western blot, ELISA, immunoprecipitation, influence on biological activity assays and immunocytochemical staining. These techniques and others are well described in the literature. (See, for example, Hurrell, J. G. R., ed., *Monoclonal Hybridoma Antibodies: Techniques and Applications,* CRC Press Inc., Boca Raton, Fla., 1982.) Hybridomas which secrete antibodies of interest are maintained in culture. The cells are expanded in culture and at the same time may be cloned in such a manner as to obtain colonies originating from single cells. This provides for the monoclonality of the antibodies obtained from the hybridomas. A wide variety of techniques exist for cloning cells, including limiting dilution, soft agar cloning and fluorescence-activated cell sorting.

Once clones of cells are obtained they are reassayed for the production of the antibody of interest. These cells are then expanded in culture to allow for the production of larger amounts of the antibody. Methods for expansion of the cells include maintaining the cells in culture, placement of the cells in a bioreactor or other type of large-scale cell culture environment, or culturing the cells using various agar or gelatin carrier matrices. Antibodies are then isolated from the cell culture media.

A preferred method for producing large amounts of antibodies involves growing the hybridoma cells in ascites fluid. The hybridomas are preferably isolated from the culture media by centrifugation and washed with an iso-osmotic solution, preferably phosphate buffered saline. The cells are then resuspended in an iso-osmotic solution and injected into the peritoneal cavity of an appropriate host animal, preferably a mouse, and allowed to grow within the host animal The host animal may receive a pre-injection of pristane (2,6,10,14-tetramethylpentadecane) prior to the injection of the hybridoma cells, preferably seven to thirty days prior to the introduction of the hybridomas. Following growth of the cells in the peritoneal cavity, ascites fluid, containing the antibody of interest, is collected.

Antibodies may be purified from conditioned media or ascites fluid by a variety of methods known in the art. These methods include ammonium sulfate precipitation, ion exchange chromatography (see Hurrell, ibid.) and high pressure liquid chromatography using a hydroxylapatite support (Stanker et al., *J. Immunol. Methods* 76:157, 1985). A preferred method for purifying antibodies from conditioned media or ascites fluid utilizes a commercially available Protein A-Sepharose CL-4B column (Pharmacia, Piscataway, N.J.; Sigma, St. Louis, MO). Antibodies may be purified with these columns using conditions suggested by the manufacturer. Typically, the conditioned medium or ascites fluid is mixed with an equal volume of TNEN (20 mM Tris-base pH 8.0, 100 mM NaCl, 1 mM $Na_2EDTA$, 0.5% NP-40) and applied to the column. The antibodies are eluted using a pH gradient. Preferably the elution buffer comprises 0.1M sodium citrate.

As noted above, the monoclonal antibodies of the present invention may be utilized within methods for purifying native PDGF or selected PDGF isoforms from a variety of samples. Within a preferred method, the monoclonal antibodies are immobilized or attached to a substrate or support material, such as polymeric tubes, beads, polysaccharide particulates, polysaccharide-containing materials, polyacrylamide or other water-insoluble polymeric materials. A particularly preferred substrate is CNBr-activated Sepharose 4B (Pharmacia, Piscataway, NJ). Methods for immobilization are well known in the art (Mosbach et al., U.S. Pat. No. 4,415,665; Clarke et al., *Methods Enzymol.* 68:436–442, 1979). A particularly preferred method of immobilization is CNBr activation. Activated substrates are commercially available from a number of suppliers, including Pharmacia (Piscataway, NJ), Pierce Chemical Co. (Rockford, IL) and Bio-Rad Laboratories (Richmond, CA). Generally, the substrate/antibody complex will be in the form of a column. The sample is then combined with the immobilized monoclonal antibody under conditions which will allow binding to occur. The substrate with immobilized antibody is first equilibrated with a buffer solution of a composition in which the antibody has been previously found to bind its ligand. The sample, in the solution used for equilibration, is then applied to the substrate/antibody complex. Where the complex is in the form of a column, it is preferred that the sample be passed over the column two or more times to permit full binding of ligand to antibody. The complex is then washed with the same solution to elute unbound material. In addition, a second wash solution may be used to minimize non-specific binding. Isolated protein may then be released or eluted through the use of conditions unfavorable to complex formation. Particularly useful methods include changes in pH, wherein the immobilized antibody has a high affinity for the PDGF isoform at a first pH and reduced affinity at a second (higher or lower) pH; changes in concentration of certain chaotropic agents; or through the use of detergents.

The use of isoform-specific antibodies permits the purification of selected PDGF isoforms from a sample. By combining antibodies, one may isolate total native PDGF. If an antibody specific for a particular isoform is not available, a two-step purification scheme may be used to purify that isoform. For example, PDGF AB isoform may be purified by first passing the sample over a column containing an antibody which specifically binds AB and BB isoforms. The bound material is then eluted and passed over a column which specifically binds the BB isoform. The unbound fraction will contain purified AB isoform which, if desired, may be concentrated according to conventional procedures. Other isoforms can be isolated in a similar manner, the specifics of which will be determined by the availability of particular antibodies.

Upon purification, the native PDGF. or PDGF isoforms may be used as therapeutic agents within wound healing compositions. Typically, the PDGF is combined with a pharmaceutically acceptable carrier or diluent, such as a microcrystalline collagen, in order to produce a wound treating salve suitable for administration directly to the wound.

The antibodies of the present invention can be used within a variety of assays for detecting the presence of native PDGF, PDGF isoforms or PDGF-like molecules. These assays will typically involve combining an antibody or antibodies with a biological sample under conditions which permit the formation of immune-complexes, followed by detecting the presence of the immune-complexes. Detection may be achieved through the use of a label attached to the monoclonal antibody or through the use of a labeled second antibody which is reactive with the monoclonal antibody, such as antibodies from another species. Alternatively, the labeled second antibody may be reactive with the antigen. A wide variety of labels may be utilized, such as radionuclides, fluorophores, enzymes and luminescers. Complexes may also be detected visually, i.e., in immunoprecipitation assays which do not require the use of a label. A variety of immunoassays are known in the art, including the double monoclonal antibody sandwich immunoassay technique of David et al. (U.S. Pat. No. 4,376,110); monoclonal-polyclonal antibody sandwich (Wide et al., in Kirkham and Hunter, eds., *Radioimmunoassay Methods,* E. and S. Livingstone, Edinburgh, 1970); the "western blot" method of Gordon et al. (U.S. Pat. No. 4,452,901); immunoprecipitation of labeled ligand (Brown et al., ibid.); enzyme-linked immunosorbant assays as described by, for example, Raines and Ross (ibid., 1982); immunocytochemical techniques, including the use of fluorochromes (Brooks et al., *Clin. Exp. Immunol.* 39: 477, 1980); and neutralization of activity (Bowen-Pope et al., *Proc. Nat'l. Acad. Sci. USA* 81: 2396–2400, 1984), all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference. A particularly preferred assay is a sandwich assay in which the PDGF isoform-specific monoclonal antibody is bound to a solid substrate, such as polymeric microtiter plate wells, and antigen or a test substance is applied to the wells to allow antibody-antigen binding. The unbound antigen is removed and a second (polyclonal) antibody which recognizes a different epitope or epitopes on the antigen is applied. Alternatively, the second antibody and the antigen are added to the wells simultaneously. The second antibody may be labeled directly (e.g., with a radioisotope or enzyme) or may be detected through the use of a labeled third antibody which recognizes the second antibody. Assays may be used to detect the presence of one or more isoforms of PDGF. Through the use of a panel of isoform-specific antibodies it is possible to detect the presence of all isoforms of native PDGF in the sample.

As noted above, the monoclonal antibodies of the present invention may be utilized within enzyme immunoassays, where the subject antibodies, or second antibodies from a different species, are conjugated to an enzyme. Briefly, when a biological sample containing native PDGF or one or more PDGF isoforms is combined with the subject antibodies, binding occurs, after which the proteins may be separated from the unbound reagents, and a second antibody (labeled with an enzyme) added. Thereafter, the presence of the antibody-enzyme conjugate specifically bound to the native PDGF or PDGF-isoform is determined. As noted above, other conventional techniques well known to those skilled in the art may also be utilized.

The antibodies of the present invention may be labeled with a radioisotope or other imaging agent and used for in vivo diagnostic purposes. Preferred radioisotope imaging agents include iodine-125 and technetium-99 with technetium-99 being particularly preferred. Methods for producing protein-isotope conjugates are well known in the art, and are described by, for example, Eckelman et al. (U.S. Pat. No. 4,652,440), Parker et al. (WO 87/05030) and Wilbur et al. (EP 203,764). Alternatively, the antibodies may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026). For administration, the labeled antibodies are combined with a pharmaceutically acceptable carrier or diluent, such as sterile saline or sterile water. Administration is preferably by bolus injection, preferably intravenously. These imaging agents are particularly useful in identifying the locations of atherosclerotic plaques, PDGF-producing tumors, and receptor-bound PDGF.

The monoclonal antibodies of the present invention may also be utilized within diagnostic kits. Briefly, the subject monoclonal antibodies are provided in a lyophilized form or immobilized onto the walls of a suitable container, either alone or in conjunction with additional antibodies capable of binding to native PDGF or a selected PDGF isoform(s). The antibodies, which may be conjugated to a label or unconjugated, are generally included in the kits with suitable buffers, such as phosphate, stabilizers, inert proteins or the like. Generally, these materials are present in less than about 5% wt. based upon the amount of active antibody, and are usually present in an amount of at least about 0.001% wt. It may also be desirable to include an inert excipient to dilute the active ingredients. Such an excipient may be present in from about 1% to 99% wt. of the total composition. In addition, the kits will typically include other standard reagents, instructions and, depending upon the nature of the label involved, reactants that are required to produce a detectable product. Where a second antibody capable of binding to the monoclonal antibody is employed, this second antibody will usually be provided in a separate vial. The second antibody is typically conjugated to a label and formulated in an analogous manner with the antibody formulations briefly described above. The diagnostic kits, including the containers, may- be produced and packaged using conventional kit manufacturing procedures.

The following examples are offered by way of illustration and not by way of limitation.

EXAMPLES

Enzymes, including restriction enzymes, DNA polymerase I (Klenow fragment), $T_4$ DNA ligase and $T_4$ polynucleotide kinase, were obtained from New England Biolabs (Beverly, MA) Bethesda Research Laboratories (Gaithesburg, Md.) and Boerhinger-Mannheim Biochemicals (Indianapolis, Ind.) and were used as directed by the manufacturer or as described in Maniatis et al. (*Molecular Cloning: A Laboratory Manual,* Cold Spring Harbor Laboratory , N.Y., 1982).

EXAMPLE I

Construction of VSB-PDGF B-Chain Analog

A. Preparation of v-sis for Fusion to MFα1

Six hundred ug of plasmid pSSV-11 (FIG. 1) was digested with restriction endonucleases Bam HI and Pvu II in 200 microliters (ul) of 50 mM NaCl, 10 mM $MgCl_2$, 10 mM Tris pH 7.5 (medium salt buffer), and 100 ug/ml bovine serum albumin (BSA), overnight at 37° C. The digestion products were electrophoresed through a 1.1% agarose gel and the 1100 base pair (bp) Bam HI-Pvu II fragment (FIG. 1) was cut out, extracted and EtOH precipitated. The DNA pellet was dissolved in 75 ul Hph I buffer to which was added 20 ul of 1 mg/ml BSA and 5 ul Hph I. After overnight digestion at 37° C. the mixture was electrophoresed through a 1.25% agarose gel and the 396 bp Hph I-Pvu II fragment was isolated from the gel and EtOH precipitated. The DNA pellet was dissolved in 30 ul of Klenow buffer (6 mM Ttis, pH 7.5, 6 mM $MgCl_2$, 60 mM NaCl) and the 3' overhanging nucleotide at the Hph I cleavage site was removed by treatment with 5 units of DNA polymerase I (Klenow fragment) for 5 minutes at 37° C. One ul of a mixture containing all four deoxyribonucleotides each at 1 mM was added and the reaction mixture was incubated an additional 10 minutes. After phenol/$CHCl_3$/ether ($Et_2O$) extraction and EtOH precipitation, the DNA pellet was dissolved in 30 ul of medium salt buffer and digested with 5 units of Bgl II for three hours at 37° C. The DNA was electrophoresed through a 1.25% agarose gel and the 269 bp Hph I–Bgl II fragment was extracted and EtOH precipitated. The Hph I cleavage terminus of this Klenow blunted fragment begins with the tri-nucleotide sequence

5'ATG...

3'TAC...

B. MFα1 Promoter and Secretory Leader Fragment

Figure 2:
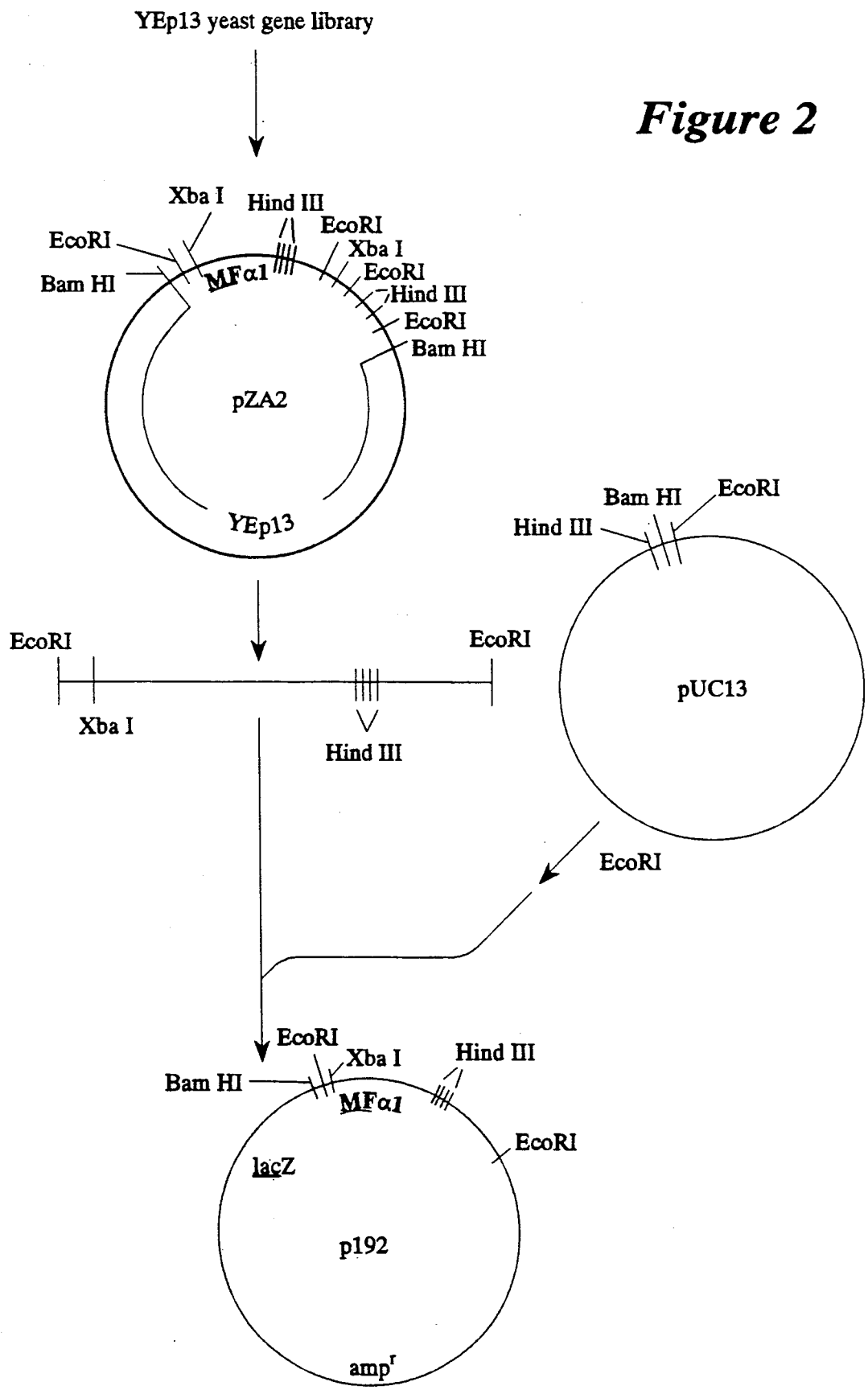
FIG. 2 illustrates the construction of plasmid p192.

Plasmid p192 (FIG. 2) comprises a portion of the gene for the yeast mating pheromone α-factor (MFα1 gene) cloned in the bacterial plasmid pUC13 (Vieira and Messing, *Gene* 19:259-268, 1982; and Messing, *Meth. in Enzymology* 101: 20-78, 1983). Cloning of the MFα1 gene from a genomic library has been described by Kurjan and Herskowitz (ibid.). The gene was isolated in this laboratory in a similar manner, using as starting material a yeast genomic library of partial Sau 3A fragments-cloned into the Bam HI site of YEp13 (Nasmyth and Tatchell, *Cell* 19: 753, 1980). From this library, a plasmid was isolated which expressed α-factor in a diploid strain of yeast homozygous for the matα2-34 mutation (Manney et al., *J. Cell Biol.* 96: 1592, 1983). The clone contained an insert overlapping with the MFα1 gene characterized by Kurjan and Herskowitz (ibid). This plasmid, known as pZA2 (FIG. 2), was cut with Eco RI and the 1700 bp fragment comprising the MFα1 gene was purified. This fragment was then subcloned into the Eco RI site of pUC13 to produce the plasmid p192.

Fifteen ug of plasmid p192 was digested in 30 ul of medium salt buffer with 20 units of Hind III overnight at 37° C. The reaction mixture was diluted to 60 ul with Klenow buffer and the four deoxyribonucleotides added to a final concentration of 50 uM each. Ten units of DNA polymerase I (Klenow fragment) was added to the ice-cold mixture and incubation was allowed to proceed for 12 minutes at 15° C. Following phenol/CHCl$_3$/Et$_2$O extraction, the aqueous phase was concentrated by lyophilization to a volume of 10 ul and digested with 20 units of Eco RI for 70 minutes at 37° C. The products were electrophoresed through a 0.9% agarose gel and the 1.2 kb Eco RI-Hind III (blunted) MFα1 fragment was extracted and EtOH precipitated. This DNA fragment contains the transcriptional promoter and secretory signal sequences of MFα1.

C. Construction of pVSα

A subclone of pSSV-11 (FIG. 1) containing a portion of the v-sis gene was constructed in the *E. coli* replicating plasmid pUC13 (Vieira and Messing, *Gene*, 19: 259, 1982; and Messing, *Methods Enzymol.* 101: 20-78, 1983). Five micrograms (ug) of pSSV-11 was digested with the restriction endonuclease Pst I and the 1.2 kb fragment was purified by agarose gel electrophoresis (0.9%) and extracted from the gel with cetyltrimethylammonium bromide (CTAB) plus butanol (Langridge et al., *Anal. Biochem.* 103 264-271, 1980). Two ug of pUC13 was also digested with Pst I, phenol/chloroform (CHCl$_3$) extracted and ethanol (EtOH) precipitated. Forty ng of the 1.2 kb v-sis fragment and 50 ng of Pst I cut pUC13 were ligated overnight at room temperature with 40 units (u) of T$_4$ DNA ligase. The ligation mixture was used to transform *E. coli* K-12 strain JM83 (Messing, Recombinant DNA Technical Bulletin, NIH Publication No. 79-009, 2, No. 2, 43-48, 1979) in the presence of 5-bromo, 4-chloro, 3-indolyl-β-D-galactoside (X-gal) and isopropyl β-D-thio-galactoside (IPTG). Plasmid DNA prepared from ampicillin resistant white colonies was digested with Pst I to verify the presence of the insert and the resulting plasmid was designated pVSIS/Pst.

Twenty ug of plasmid pVSIS/Pst was digested with Bgl II and Xba I in 40 ul of medium salt buffer. Subsequent electrophoresis through 1% agarose, extraction of the DNA and EtOH precipitation provided the purified v-sis 756 bp Bgl II-Xba I fragment (FIG. 1). *E. coli* replicating plasmid pUC12 (5 ug) was digested with Eco RI and Xba I and gel purified as above (FIG. 1).

Referring to FIG. 1, equimolar amounts of the four DNA fragments described above (blunted Mfaal from p192, blunted v-sis from pSSV-11, Bgl II-Xba I v-sis from pVSIS/Pst and Xba I-Eco RI pUC12), adjusted to 10 ng of the pSSV-11 v-sis fragment, were mixed in 15 ul of ligase buffer (6 mM Tris pH 7.6, 6.6 mM Mgl$_2$, 0.4 mM ATP, 2 mM spermidine, 20 mM DTT, and 100 ug/ml BSA) and ligated with 40 units of T$_4$ DNA ligase overnight at 14° C. The reaction mixture was brought to room temperature, an additional 150 units of T$_4$ DNA ligase was added, and the mixture was incubated 10 more hours. Seven ul of the ligation mix was used to transform *E. coli* K-12 RR1 (ATCC #31343; Bolivar, ibid.) and ampicillin-resistant transformants were selected. Plasmid DNA was prepared from 12 such bacterial colonies and digested with Xba I. Two clones gave a 2.2 kb band predicted by the proper fragment alignment (FIG. 1). Further analysis of these clones by Bgl II-Xba I restriction mapping gave expected bands of approximately 1.5 kb from the MFα1/v-sis fusion and 760 bp for the Bgl II-Xba I v-sis fragment. DNA sequence analysis verified the desired nucleotide sequence at the MFα1/v-sis junction. The resultant plasmid was designated pVSα.

D. Oligonucleotide-Directed Deletion Mutagenesis of 66 Amino Terminal v-sis Codons Homology between the v-sis protein p28$^{sis}$ and PDGF begins at amino acid 67 of p28$^{sis}$, a serine residue corresponding to the NH$_2$-terminal residue of the PDGF B-chain (Johnsson, ibid., 1984)

Proteolytic processing of the MFα1 primary translation product occurs at the Lys-Arg cleavage signal 85 amino acids from the initiator methionine (Kurjan and Herskowitz, ibid.). A v-sis derivative was constructed in which the first 66 codons of p28$^{sis}$ were removed such that serine residue 67 of v-sis immediately follows the MFα1 Lys-Arg processing signal.

Figure 3:
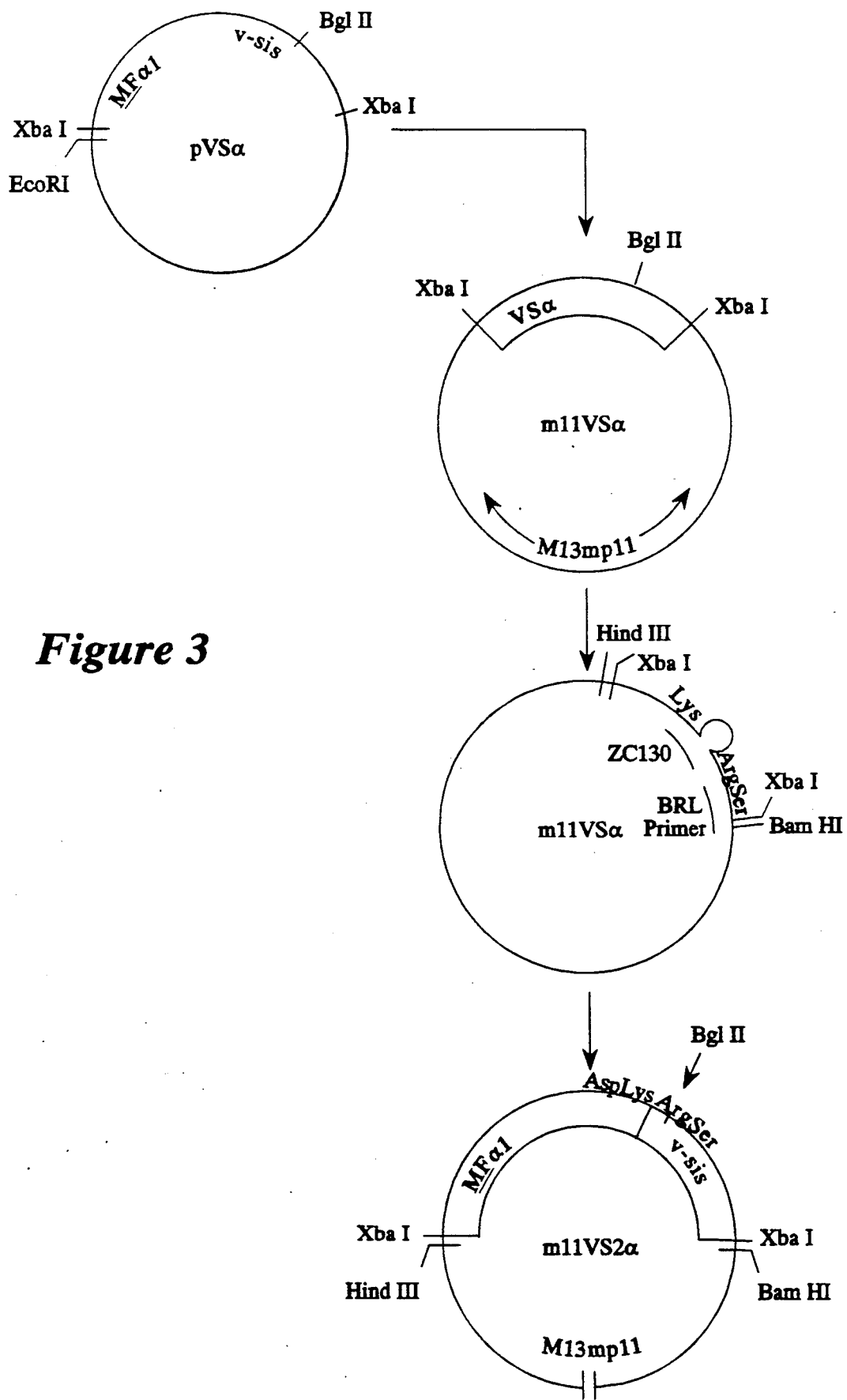
FIG. 3 illustrates the oligonucleotide-directed deletion mutagenesis of the amino-terminal sixty-six v-sis codons.

Referring to FIG. 3, approximately 40 ng of the gel purified 2.2 kb Xba I fragment of pVSα was ligated with 120 ng of Xba I digested, alkaline phosphatase treated M13mp11 DNA (Messing, ibid.). The ligation mixture was used to transform *E. coli* K 12 strain JM101 (ATCC 33876) in the presence of X-gal and IPTG. Isolated white plaques were picked and used to infect 3 ml cultures of log phase JM101 cells. Replicative form (RF) DNA was prepared and clones which carried the insert fragment in the same orientation as the positive (+) strand form of the single-stranded mature phage were identified. Single-stranded phage DNA was prepared from one such clone and designated m11VSα.

To precisely remove codons 1-66 of v-sis, oligonucleotide-directed mutagenesis was performed essentially according to the two primer method of Zoller (Zoller et al., *Manual for Advanced Techniques in Molecular Cloning Course*, Cold Spring Harbor Laboratory, N.Y., 1983; Zoller and Smith, *DNA* 3:479-488, 1984).

Oligonucleotide ZC130 (3' AGAAACC-TATTTTCCTCGGACCCA 5') was synthesized on an Applied Biosystems 380-A DNA synthesizer. Fifty pmoles of ZC130 was kinased in 10 ul of kinase buffer (BRL) with 4 units of $T_4$ polynucleotide kinase for 45 minutes at 37° C. The enzyme was inactivated by heating at 65° C for 10 minutes.

One-half pmole of mIIVSa was annealed with 1 pmole of kinased ZC130 and 1.5 pmoles of universal sequencing primer (BRL) using standard conditions, except that the annealing mixture was first heated to 65° C. for 10 minutes, shifted to 37° C. for 10 minutes, and then quickly chilled on ice. The annealed mixture was then treated with DNA polymerase I (Klenow fragment) to create circular duplex DNA. Portions of the elongation mixture were used to transform E. coli K12 JM101 cells. The resulting phage plaques were screened for the proper deletion by transfer onto nitrocellulose filters and subsequent hybridization with 32P phosphorylated ZC130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and RF DNA was prepared for restriction enzyme analysis. Five isolates showed the expected decrease in size of 195 bp to the 1450 bp Hind III-Bgl II fragment (FIG. 3). DNA sequence analysis of two isolates confirmed the correct fusion junction had been made, thus maintaining the proper translational reading frame. One of these phage was designated mIIVS2a.

E. Construction of Plasmids YEpVSα and YEpVS2α

The yeast/*E. coli* shuttle vector YEp13 (Broach et al., ibid.) was used as an expression vehicle for v-sis derived constructions described above. YEp13 is a multicopy extrachromosomal plasmid containing a 2 micron replication origin and the yeast LEU2 gene. This allows for selection of the plasmid in yeast strains possessing a defective chromosomal LEU2 gene when grown on synthetic medium lacking leucine. Addition of yeast terminator sequences to foreign genes expressed in yeast ensures efficient transcription termination and polyadenylation of mRNA. The v-sis expression units VSα and VS2α were placed adjacent to the TPI1 terminator fragment which was previously cloned into YEp13 (below).

Figure 4:
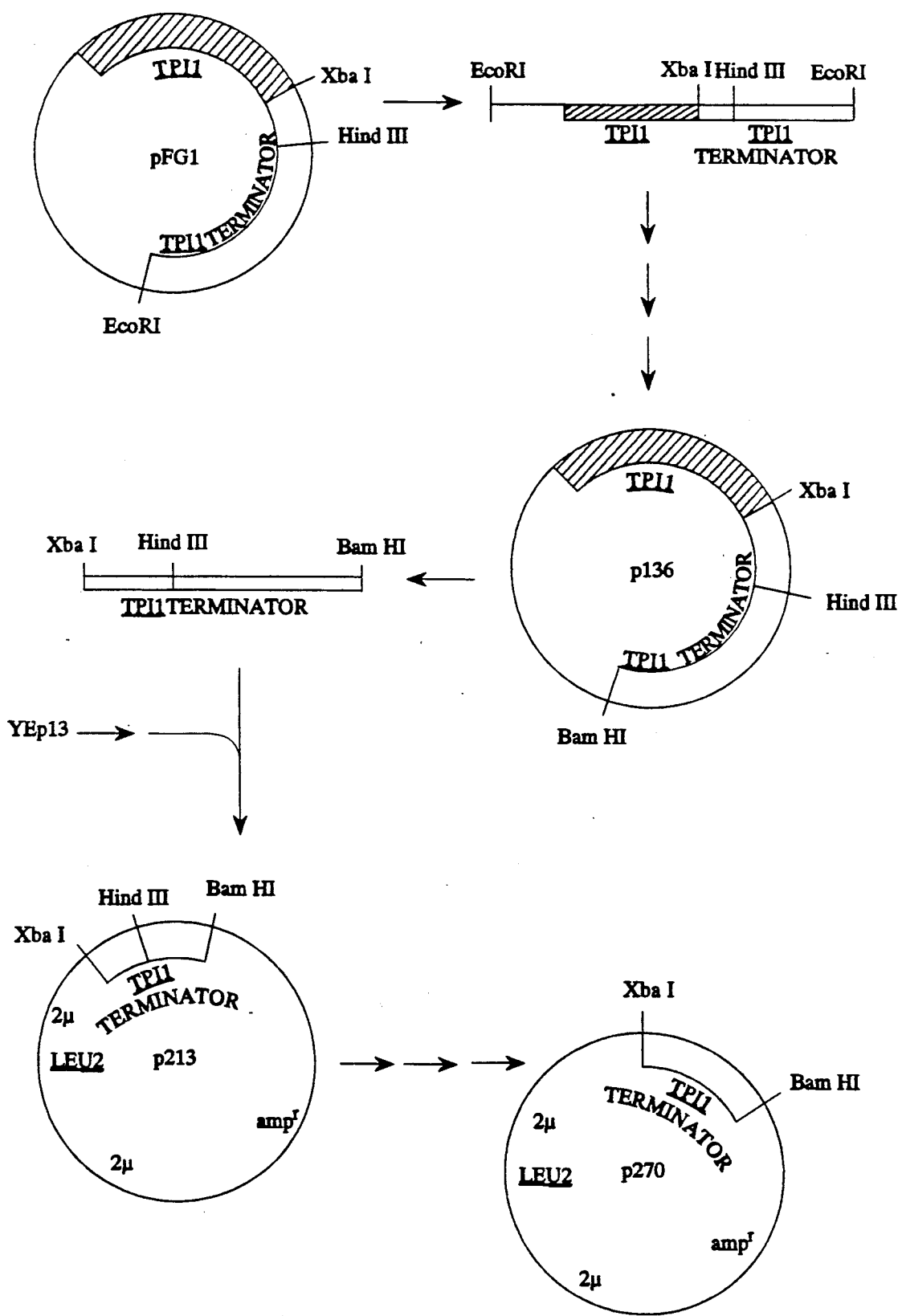
FIG. 4 illustrates the construction of plasmid p270.

Plasmid p270 (see FIG. 4) contains the transcription terminator region of the yeast triose phosphate isomerase (TpI1) gene. It was constructed in the following manner. The yeast TPI1 terminator fragment was obtained from plasmid pFG1 (Alber and Kawasaki, ibid.). It encompasses the region from the penultimate amino acid codon of the TPI1 gene to the Eco RI site approximately 700 base pairs downstream. A Bam HI site was substituted for this unique Eco RI site of pFG1 by first cutting the plasmid with Eco RI, then blunting the ends with DNA polymerase I (Klenow fragment), adding synthetic Bam HI linkers (CGGATCCA), and re-ligating to produce plasmid p136. The TPI1 terminator was then excised from p136 as a Xba I-Bam HI fragment. This fragment was ligated into YEp13 (Broach et al., ibid.) which had been linearized with Xba I and Bam HI. The resulting plasmid is known as p213. The Hind III site was then removed from the TPI1 terminator region of p213 by digesting the plasmid with Hind III, blunting the resultant termini with DNA polymerase I (Klenow fragment), and recircularizing the linear molecule using $T_4$ DNA ligase. The resulting plasmid is p270.

Alternatively, p270 may be constructed by digesting plasmid pM220 (deposited with ATCC as an *E. coli* RRI transformant under accession number 39853) with Xba I and Bam HI, purifying the TPI1 terminator fragment (~700 bp) and inserting this fragment into XbaI and Bam HI digested YEp13.

Figure 5:
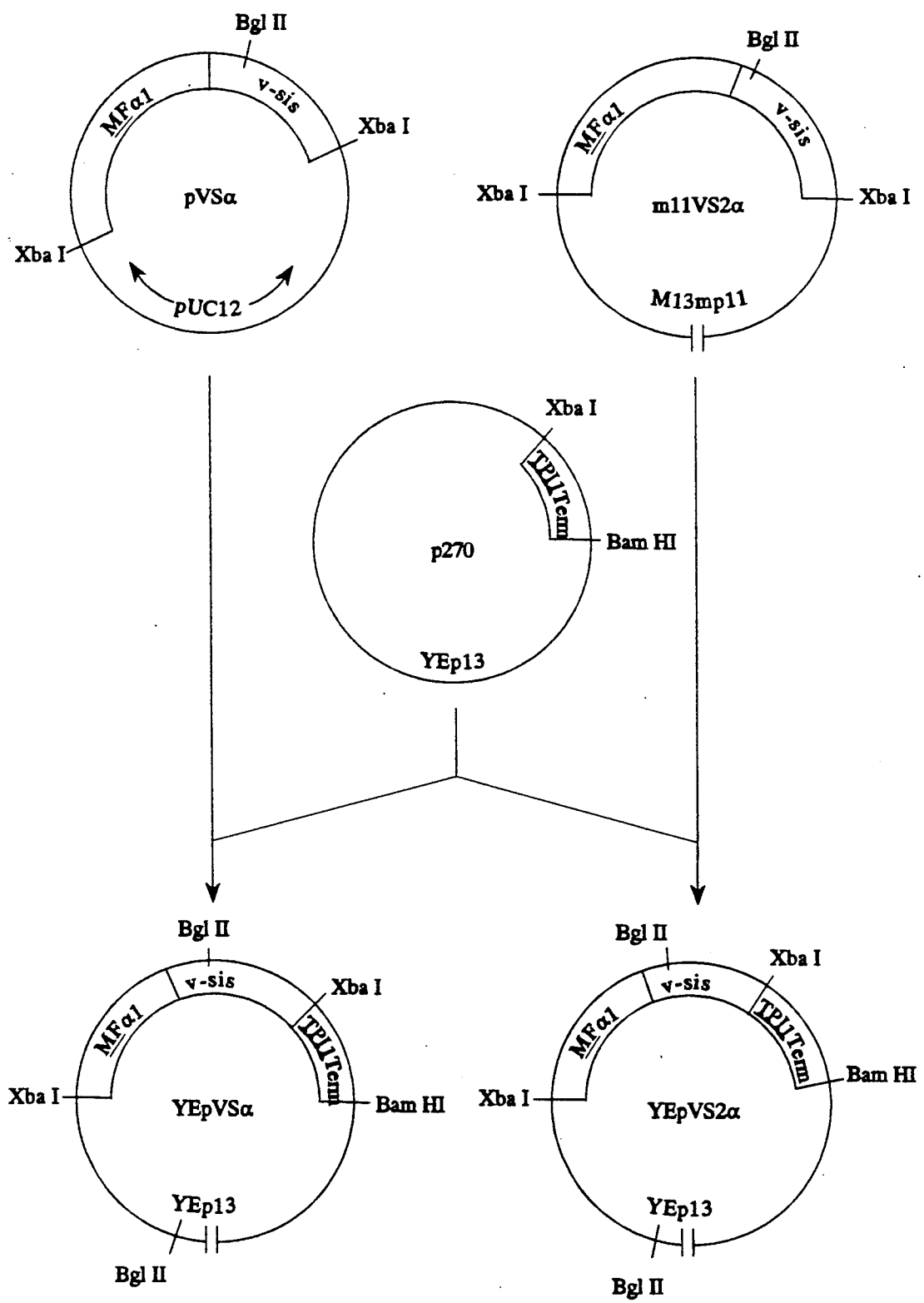
FIG. 5 illustrates the insertion of v-sis expression units upstream of the TPI1 terminator.

Referring to FIG. 5, plasmid p270 DNA was digested with Xba I and treated with calf alkaline phosphatase to prevent religation of the cohesive vector ends V-sis expression units VSα and VS2α were prepared by Xba I digestion and agarose gel purification of pVSα and mIIvs2α, respectively. Each of the isolated fragments was ligated with an approximately equimolar amount of phosphatased p270 vector in the presence of 40 units of $T_4$ DNA ligase and the ligation mixtures were transformed into *E. coli* K-12 RR1. Plasmid DNA was prepared from ampicillin-resistant colonies and restriction enzyme analysis performed in order to identify clones which possessed the TPI1 terminator adjacent to 3' v-sis sequences. Presence of 3.3 kb or 3.1 kb Bgl II fragments after gel electrophoresis indicated the correct orientation of YEpVSα and YEpVS2α, respectively.

F. Construction of Plasmid pVSB

Because the product encoded by YEpVS2α is larger than authentic human PDGF B-chain, a vector was constructed comprising the v-sis sequence of YEpVS2α truncated at the 3' end. The polypeptide encoded by this sequence comprises amino acids 67 to 175 of $p28^{sis}$ and is homologous to the B-chain of PDGF.

Figure 6:
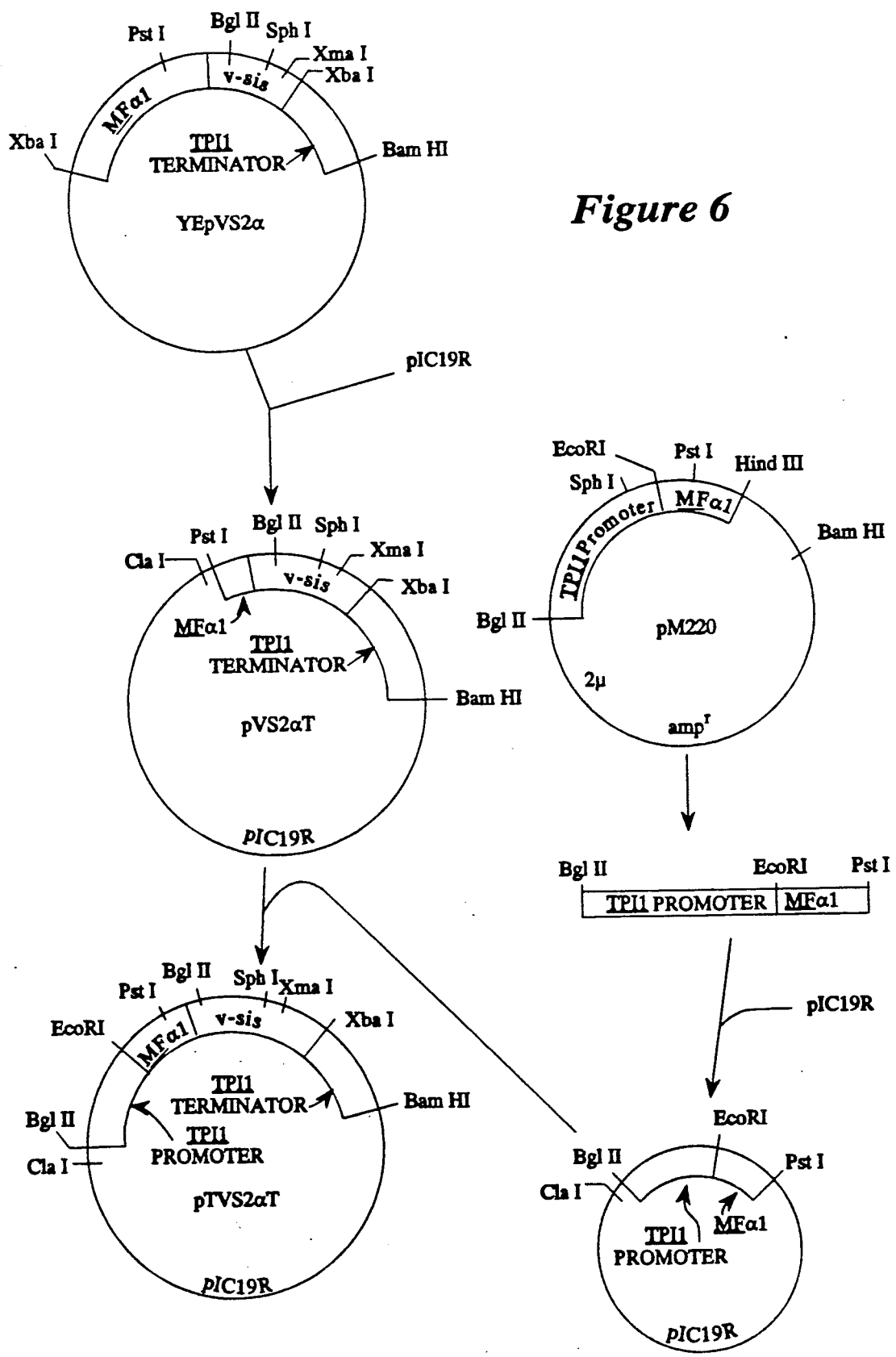
FIG. 6 illustrates the construction of pTVS2αT.
Figure 7:
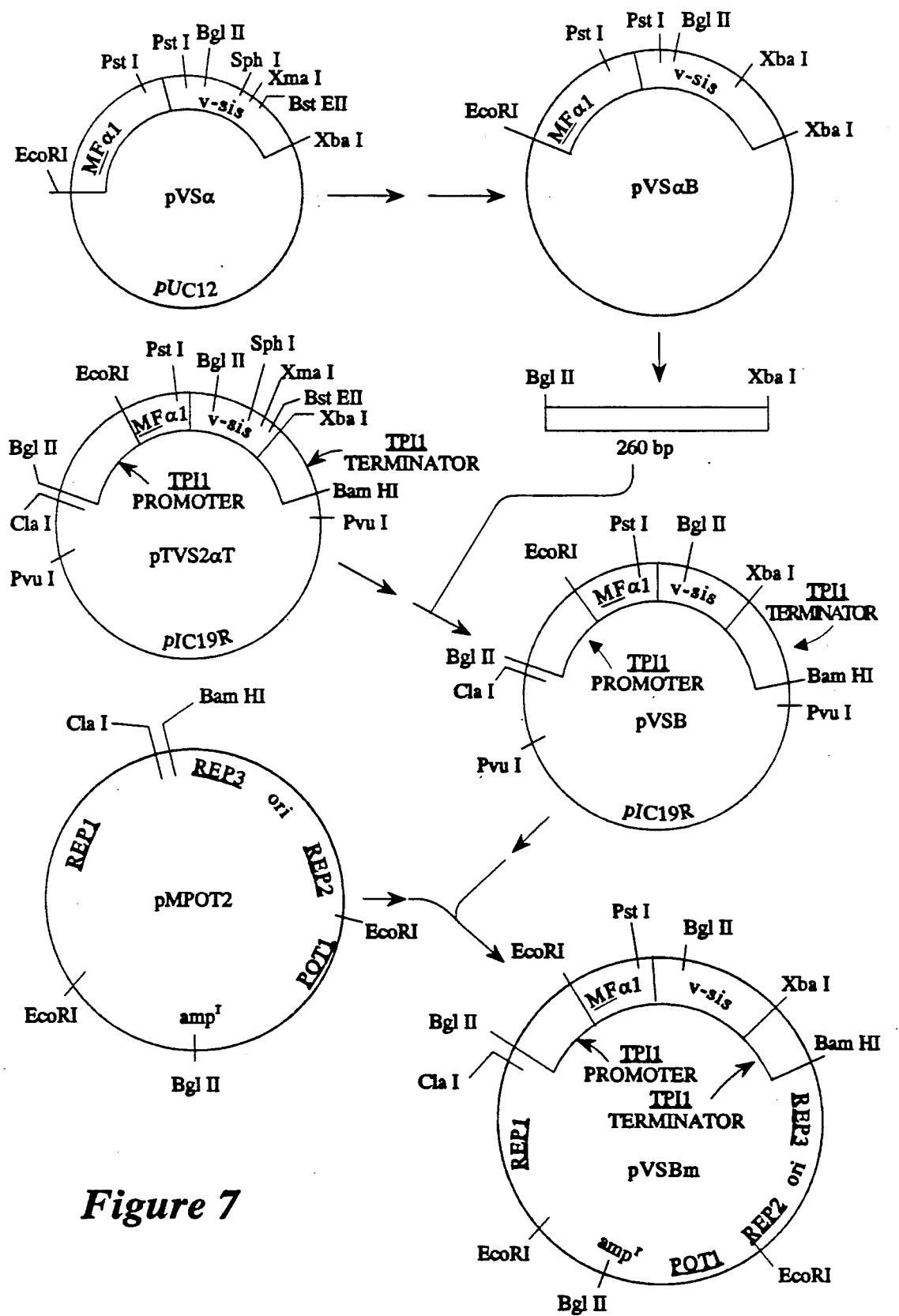
FIG. 7 illustrates the construction of a B-chain expression unit VSB and its introduction into the pMPOT2 vector.

An expression vector containing this B-chain sequence was constructed by combining elements of the YEpVS2α expression unit with a partial v-sis gene and a synthetic double-stranded DNA fragment encoding amino acids 158 to 175 of $p28^{sis}$. This synthetic fragment was designed to substitute preferred yeast codons for many of the 13 v-sis codons it replaces, and to supply a stop codon at the end of the coding sequence. The construction of this vector is illustrated in FIGS. 6 and 7.

Plasmid YEpVS2α was digested with Pst I and Bam HI and the 1.8 kb fragment comprising the partial MFα1 sequence, v-sis, and TPI1 terminator sequences was purified by agarose gel electrophoresis. Plasmid pIC19R (Marsh et al. *Gene* 32:481-485, 1984) was digested with Pst I and Bam HI, and the vector fragment was gel purified and joined to the 1.8 kb fragment from pVS2α to produce plasmid pVS2αT.

plasmid pM220 was digested with Bgl II and pst I, and the ca. 1 kb fragment comprising the TPI1 promoter and the 5= portion of the MFα1 sequence was isolated and cloned in Bgl II+Pst I digested pIC19R. The resultant plasmid was digested with Cla I and Pst I, and the TPI1 promoter - MFα1 fragment was gel purified. Plasmid pVS2αT was then cut with Cla I and Pst I and joined to the TPI1 promoter - MFα1 fragment. The correct construct was identified by the presence of a 2.6 kb Cla I - Bam HI fragment and was designated pTVS2αT.

Ten ug of plasmid pVSα was digested with Xma I and Sph I to completion. The resulting ca. 4.9 kb vector fragment, which also comprises most of the v-sis sequence, was purified by agarose gel electrophoresis, extraction of the DNA and EtOH precipitation.

In order to supply a new 3' terminus for the v-sis sequence, a double-stranded DNA fragment was constructed from oligonucleotides synthesized on an Applied Biosystems Model 380-A DNA synthesizer. ~0.7 pmole of oligonucleotide ZC299 (Table 1) was heated with an equimolar amount of oligonucleotide ZC300 in a volume of 10 ul containing 40 mM NaCl for 5 minutes at 65° C.

TABLE 1

ZC299: 5'TAAG TGT GAA ATC GTT GCC GCG GCT AGA GCT GTT ACC TAA TCT AGA3'
ZC300: 3'GTACA TTC ACA CTT TAG CAA CGG CGC CGA TCT CGA CAA TGG ATT AGA TCT GGCC5'

The mixture was then incubated at 37° C. for 5 minutes and allowed to cool to room temperature. 0.2 pmole of the purified 4.9 kb vector fragment was added, the mixture ligated for 18 hours at 12° C. and used to transform E. coli HB101 (ATCC 33694) to ampicillin resistance. DNA was prepared from ampicillin-resistant colonies and digested with Bgl II and Xba I. After electrophoresis through agarose, the desired clone (known as pVSαB) was identified by loss of a ca. 750 bp Bgl II-Xba I fragment and appearance of two smaller fragments of approximately 500 and 260 bp.

Approximately 8 ug of plasmid pTVS2αT was digested to completion with Xba I in a volume of 10 ul. The volume was increased to 40 ul with Bgl II buffer, and 6 units of Bgl II was added and the mixture was incubated at 37° C. Ten ul aliquots were removed to a stop buffer containing 50 mM EDTA at 15 and 30 minutes, and the remaining 20 ul stopped at 45 minutes. The resulting mixtures were separated by electrophoresis through a 0.7% agarose gel. The ca. 4.6 kb Bgl II-Xba I vector fragment was cut out, extracted from the gel, and EtOH precipitated. Plasmid pVSαB was digested with BglII and Xba I, and the ca. 260 bp fragment containing the synthetic 3' terminus and stop codon was isolated by electrophoresis through agarose, subsequent extraction from the gel, and EtOH precipitation.

The 4.6 kb Bgl II-Xba I vector fragment from pTVS2αT and the 260 bp Bgl II-Xba I fragment from pVSαB were ligated in the presence of T4 DNA ligase for 7 hours at room temperature. The reaction mixture was used to transform E. coli HB101 to ampicillin resistance. DNA was prepared from transformants and the presence of the desired insert was confirmed by screening for a 550 bp Pst I-Xba I band on an agarose gel. A plasmid having the correct configuration was designated pVSB (FIG. 7).

EXAMPLE II

Construction of A-Chain Vector pA7

A. Construction of pSB1

In order to begin replacing B-chain coding sequence with A-chain sequence in the pVSB vector, a convenient Sst I restriction endonuclease site was created close to the α-factor prepro-B-chain boundary (FIG. 7). This was accomplished by oligonucleotide-directed mutagenesis on a single-stranded pVSB template using established techniques (Zoller et al., ibid.; Zoller and Smith, ibid.). The mutagenic oligonucleotide used is termed ZC506 and can be seen in Table 2.

TABLE 2

| | |
|---|---|
| ZC506 | GGCTCCTTTTGAGCTCAGATACCCCT |
| ZC545 | GATCTCGTAGATAACGGTACGCGTCTTACAAACAGCTCTCTTGAGCT |
| ZC546 | CAAGAGAGCTGTTTGTAAGACGCGTACCGTTATCTACGA |
| ZC547 | CAAGAGATCTATCGAAGAAGCGGTACCAGCCGTTTGTAAGACGCGTGA |
| ZC548 | GATCTCACGCGTCTTACAAACGGCTGGTACCGCTTCTTCGATAGATCT CTTGAGCT |
| ZC692 | GATCCCAAGATCCCAAGTTGACCCAACCTCTGCCAACTTC |
| ZC693 | TTGGCAGAGGTTGGGTCAACTTGGGATCTTGG |
| ZC746 | TTGATTTGGCCACCATGTGTTGAAGTTAAGAGATGTACTGGGTGT |
| ZC747 | CAGTACATCTCTTAACTTCAACACATGGTGGCCAAATCAAGAAG |
| ZC748 | TGTCAAACCTCGAGTGTTAAGTGTCAACCATCCAGAGT |
| ZC749 | GATGGTTGACACTTAACACTCGAGGTTTGACAACACC |
| ZC750 | TCACCACAGATCCGTTAAGGTTGCCAAGGTTGAATACGTTAGAAAGAA GCCAA |
| ZC751 | AGCTTTGGCTTCTTTCTAACGTATTCAACCTTGGCAACCTTAACGGAT CTGTGGTGAACTCTG |
| ZC752 | AGCTTAAGGAAGTTCAAGTTAGATTGGAAGAACACTTGGAATGTGCAT GCGCTACCACCTCTTTGAACCCAGACTACAGAGAATAAT |
| ZC753 | CTAGATTATTCTCTGTAGTCTGGGTTCAAAGAGGTGGTAGCGCATGCA CATTCCAAGTGTTCTTCCAATCTAACTTGAACTTCCTTA |

A Pst I-Xba I fragment of pVSB (FIG. 7) was subcloned into the phage vector M13mp19. Single-stranded template DNA was prepared from *E. coli* JM107 cultures infected with this recombinant phage and used in the following mutagenesis reaction. Five ul of M13 template DNA (0.5 picomole) was combined with 2 ul of oligonucleotide ZC506 (1.8 pmole) plus 2.5 ul of water and 1.5 ul of 10X annealing buffer A (0.2 M Tris-HCl, 0.1M $MgCl_2$, 0.01M DTT pH 7.5; Zoller and Smith, ibid.). This mixture was annealed by heating to 70° C. for 5 minutes, cooled slowly to room temperature and then placed on ice. To this cold annealing mixture was added 1.5 ul of 10X elongation buffer B (0.2 M Tris-HCl, 0.1M $MgCl_2$, 0.1M DTT pH 7.5, Zoller and Smith, ibid.), 6 ul of deoxynucleotide triphosphates (2 5 mM each dNTP), 1 ul of $T_4$ DNA ligase, 1 ul of DNA polymerase I (Klenow fragment), 1 ul of ATP (10 mM), and 5 ul of water. This mixture was incubated for 16 hours at 18° C. This reaction mixture was then diluted 20-fold with water, and 2 ul of the dilute mixture was used to transform *E. coli* JM107 cells. The resulting phage plaques were transferred to nitrocellulose discs by the procedure of Benton and Davis (*Science* 196:180, 1977) and screened with $^{32}$P-labeled ZC506 which was labeled with $T_4$ polynucleotide kinase under standard conditions. The hybridization of the $^{32}$P-ZC506 to the filters was performed at 37° C. in 6X SSC (0.9M NaCl, 0.09M Na Citrate, pH 7.2), 100 ug/ml carrier DNA, 0.05% sodium pyrophosphate. Following hybridization, the filters were washed at 54° C. in 6×SSC, 0.1% SDS. Phage plaques giving strong autoradiographic signals were picked and RF DNA made and analyzed for the presence of a new Sst I restriction endonuclease site. The sequence around the Sst I site was also confirmed by DNA sequence analysis. The pst I-Xba I subclone now containing an Sst I site was ligated back into Pst I-Xba I digested pVSB and the resulting plasmid termed pSB1. Plasmid pSB1 encodes two amino acid changes (Leu to Glu and Asp to Leu) in the alpha-factor leader just upstream of the Lys-Arg. The resulting junction sequence is: α-factor . . . Glu Leu Lys Arg Ser . . . B-chain. The B-chain coding sequences of pSB1 are thus flanked by an Sst I site at the 5' end and an Xba I site at the 3' end.

B. Synthesis of the A-chain Amino Terminus

Figure 8:
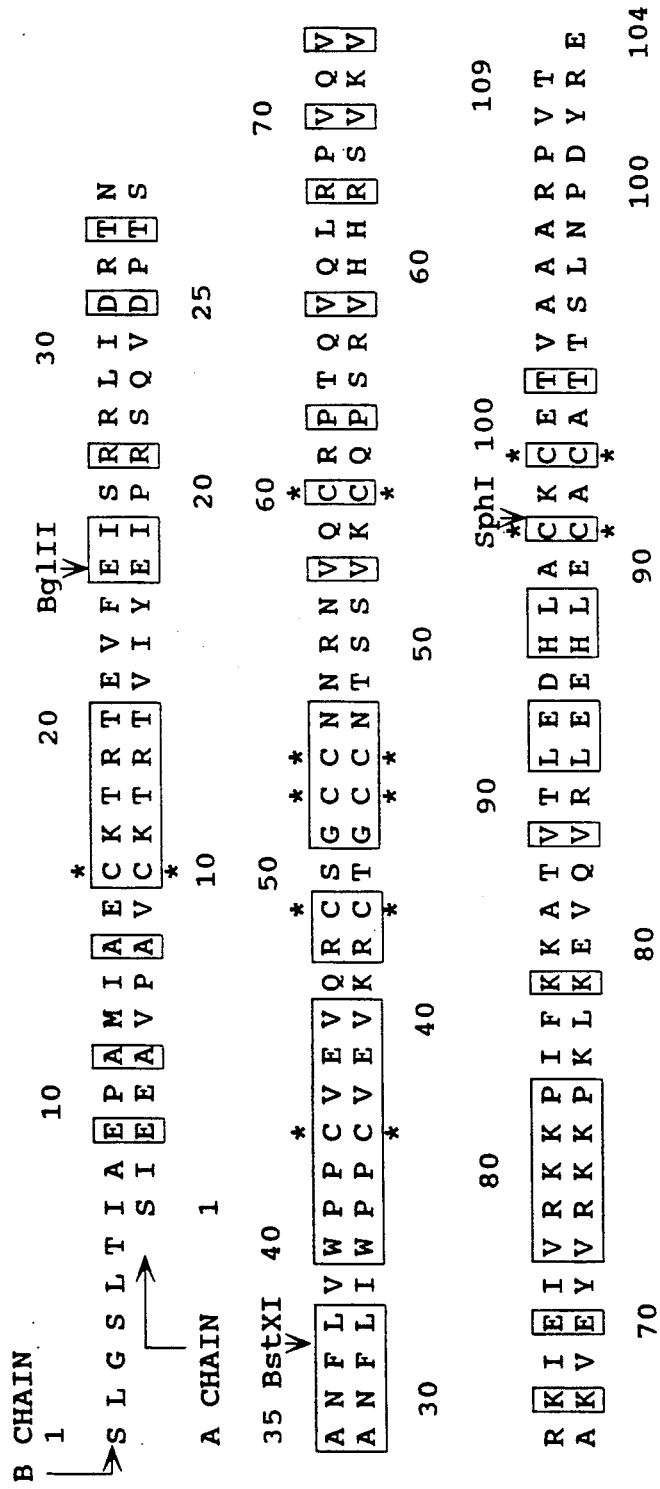
FIG. 8 illustrates the amino acid sequences of the mature A- and B-chains of PDGF.

The A-chain coding sequences were inserted into the pSB1 vector as short synthetic oligonucleotide duplexes designed to encode known A-chain amino acid sequence (Johnsson et al., ibid., 1984). ZC545 and ZC546 (Table 2) were annealed, creating a short duplex DNA fragment with a 5' Sst I cohesive end, a unique Mlu I restriction site, and a 3' Bgl II cohesive end. This duplex was cloned into Sst I and Bgl II digested pSB1. One ul of pSB1 vector (0.15 pmole) was combined with 1 ul of ZC546 (~1.6 pmole) and 0.6 ul of ZC545 (~1.5 pmole), plus 0.25 ul of 0.3 M NaCl (final NaCl concentration in the annealing reaction was 30 mM) and the mixture was heated to 60° C. for five minutes. After heating, the mixture was brought to room temperature and then placed on ice. Then 0.5 ul of 10X ligase buffer (0.5M Tris-HCl, 0.1M $MgCl_2$, 2M DTT, 0.01M ATP, pH 7.8), 0.1 ul of $T_4$ DNA ligase (New England Biolabs) and 2.5 ul of water were added and this ligation mixture was diluted and used to transform E. coli HB101 cells. Ampicillin-resistant, plasmid-bearing colonies were picked, grown up and plasmid DNA isolated by the "miniprep" method of Ish-Horowicz and Burke (Nuc. Acid Res. 9:2989-2998, 1981). The plasmids were analyzed for the presence of an Sst I-Bgl II insert and a new Mlu I restriction site and confirmed by DNA sequence analysis The ZC545-ZC546 duplex encoded A-chain amino acids alanine 8 through tryosine 17 (FIG. 8) and the resulting plasmid was termed pA1.

ZC547 and ZC548 (Table 2) were annealed to create a second short Sst I-Bgl II fragment encoding A-chain amino acids serine 1 through arginine 13 (FIG. 8) and also containing an Mlu I restriction site. The ZC547-ZC548 duplex was separately cloned into Sst I and Bgl II digested pSB1. One ul of pSB1 (1.5 pmole) digested with Sst I and Bgl II was combined with 2 ul of ZC547 (1 pmole) and 2 ul of ZC548 (1 pmole) plus 0.25 ul of 0.3 M NaCl and the mixture was heated to 50° C. for five minutes. After heating, this annealing mixture was brought to room temperature and then placed on ice. Then 0.6 ul of 10X ligase buffer and 0.1 ul of $T_4$ DNA ligase (New England Biolabs) were added and the reaction was incubated overnight at 12° C. An aliquot of this ligation reaction was diluted and used to transform E. coli HB101 cells and the resulting transformants were screened and analyzed as described above for pA1. In this case, the resulting plasmid was termed pA2.

The overlapping pA1 and pA2 A chain coding regions were joined at the unique Mlu I restriction site using conventional techniques. Plasmid pA2 was digested with Mlu I and Bam HI and the ~1.4 kb vector (pUC containing) fragment was isolated by agarose gel electrophoresis and extracted from the agarose with CTAB (Langridge et al., ibid.). Plasmid pA1 was also digested with Mlu I and Bam HI and the ~800 base pair fragment, encoding A-chain amino acids 13 through 17 fused to B-chain amino acids 24 through 109 followed by the TPI1 terminator, was isolated and extracted as above. Equimolar amounts of these two fragments were ligated under standard conditions and an aliquot was used to transform E. coli HB101 cells. Plasmids obtained from ampicillin-resistant colonies were analyzed by restriction enzyme digestion for the correct fragments and confirmed by DNA sequencing. The resulting plasmid, termed pA3, thus encoded a hybrid protein beginning with A-chain amino acids 1 through 17 followed in frame by B-chain amino acids 24 through 109.

Further addition of A-chain amino acids to the A-B hybrid was accomplished in a similar fashion. plasmid pA3 was digested first with Asp718, which cuts the plasmid once in the A-chain sequence at proline codon 7, and with Bam HI, and the A-B hybrid fragment was subcloned into pUC118. This subclone was termed pA3N and was subsequently digested with Bgl II and Bst XI. Bgl II cuts at the boundary of the A- and B-chain sequences in the hybrid and Bst XI cuts approximately 40 base pairs downstream in the B-chain. The vector fragment (pUC containing) from this digest was isolated by agarose gel electrophoresis and extracted with CTAB. One picomole each of oligonucleotides ZC692 and ZC693 (Table 2) was annealed to form a short DNA duplex with a 5' Bgl II end and a 3' Bst XI end. This duplex encoded A-chain glutamic acid 18 through phenylanine 31 and was ligated with 0.1 picomole of Bgl II-Bst XI digested pA3N. The ligation was performed overnight and the ligated products were transformed into E. coli MV1193 cells. The resulting plasmid, termed pA6N, encodes the A-chain amino acid sequence to the Bst XI site at amino acid A31 followed by B-chain amino acids B38 through B109.

C. Complete Synthesis of the A-chain Gene

The remainder of the A-chain gene was synthesized with unique restriction sites introduced in order to facilitate subcloning and sequencing the synthetic oligonucleotide sequences. The oligonucleotides were designed to reflect optimal codon usage for Saccharomyces cerevisiae.

Oligonucleotides ZC752 and ZC753 (Table 2), each 87 mers, were annealed and subcloned as a Hind III-Xba I fragment encoding A-chain amino acids 77-104 ZC752 and ZC753 (1.25 pmole each) were annealed in 5 ul of 40 mM NaCl by heating to 65° C. for 15 minutes and then allowing the mixture to come to room temperature and putting it on ice. One tenth of this annealed duplex (0.0125 pmole) was ligated into both pUC118 (0.07 pmole) and M13mp18 (0.02 pmole) which were previously digested with Hind III and Xba I. The ligated mixtures were used to transform the appropriate E. coli host strain (JM107 in the case of M13mp18 and MV1193 in the case of pUC118) and the resulting plasmid or RF DNAs were analyzed by restriction endonuclease digestion and DNA sequencing.

The oligonucleotides ZC746+747, 748+749, and 750+751 (Table 2) were designed to form short duplexes with cohesive ends which when joined would constitute the sequence between the Bst XI site at A31 and the Hind III site at A77. The oligonucleotides were phosphorylated with $^{32}P$ and $T_4$ polynucleotide kinase under standard conditions. The pairs ZC746+ZC747, ZC748+ZC749, and ZC750+ZC751 were each annealed by combining 2.5 pmole of each oligonucleotide in 5 ul of 40 mM NaCl, heating to 65° C. for 15 minutes, allowing the mixtures to come to room temperature, and putting them on ice. The three annealing mixtures were combined (now 15 ul) and ligated in a final volume of 20 ul. The ligated products were electrophoresed in a 4% NuSieve agarose gel (FMC Corporation) in TBE buffer (90 mM Tris, 90 mM boric acid, 2 mM disodium EDTA) followed by autoradiography. The ~140 base pair fragment corresponding to the three correctly ligated duplexes was cut out of the gel and extracted with CTAB. This fragment, together with the previously cloned Hind III Xba I fragment, was ligated into the Bst XI-Xba I digested pA6N vector. The resulting plasmid was termed pA6N+. Plasmid pA6N+ was then digested with Asp718 and Xba I and the A-chain coding fragment was cloned back into pA3. The resulting plasmid, designated pA7, encodes the entire mature A-chain of PDGF.

EXAMPLE III

Insertion of Expression Unit Constructions into pMPOT2

A. Construction of pMPOT2.

For expression of the PDGF isoforms in yeast, a stable expression vector comprising the REP1, REP2, REP3 and ori sequences from yeast 2 micron DNA and the *Schizosaccharomyces pombe* triose phosphate isomerase (pOT1) gene was constructed The POT1 gene provides for plasmid maintenance in a transformed yeast host grown in complex media if such host is defective for triose phosphate isomerase.

The POT1 gene was obtained from the plasmid pFATPOT. *S. cerevisiae* strain E18 transformed with pFATPOT has been deposited with ATCC under accession number 20699. The plasmid may be purified from the host cells by conventional techniques. The pOT1 sequence was removed from pFATPOT by digestion of the plasmid with Sal I and Bam HI. This 1600 bp fragment was then ligated to pIC19R, which had first been linearized by digestion with Sal I and Bam HI. The Bam HI, Pst I and Sal I sites in the resultant plasmid were destroyed in two steps to produce plasmid pICPOT*. The pst I and Sal I sites were removed by cutting with Pst I and Sal I; the ends were blunted by digesting the pst I 3' overhang with DNA polymerase 1 (Klenow fragment) and filling in the Sal I 5' overhang with DNA polmerase I (Klenow fragment). The blunt ends were then ligated. The Bam HI site was then removed by cutting the plasmid with Bam HI, filling in the ends with DNA polymerase I (Klenow fragment) and religating the blunt ends.

The 2 micron sequences were obtained from the plasmids YEp13 (Broach et al., ibid.) and Cl/1. Cl/1 was constructed from pJDB248 (Beggs, ibid ) by removal of the pMB9 sequences by partial digestion with Eco RI and replacement by Eco RI-cut pBR322. The REP3 and ori sequences were removed from YEp13 by digestion with Pst I and Xba I and gel purification. REP2 was obtained from Cl/1 by digestion with Xba I and Sph I and gel purification. The two fragments were then joined to pUC18 (Norrander et al., *Gene* 26: 101-106, 1983) which had been linearized with Pst I and Sph I to produce plasmid pUCREP2,3. REP1 was obtained from Cl/1 by digestion with Eco RI and Xba I and gel purification of the 1704 bp fragment The Eco RI-Xba I fragment was cloned into pUC13 which had been linearized with Eco RI and Xba I. The resultant plasmid was designated pUC13+REP1. The pUC13-+REP1 plasmid was cut with Hinc II and ligated in the presence of Eco RI linkers (obtained from Bethesda Research Laboratories). The REP1 gene was then removed as an Eco RI fragment of approximately 1720 bp. This Eco RI fragment was cloned into pIC7 (Marsh et al., ibid.), which had been linearized with Eco RI. The resultant plasmid was designated pICREpl#9.

To construct the final expression vector pMPOT2 (FIG. 7), pICPOT* was linearized by a partial Hind III digestion and complete Sst I digestion. Plasmid pUCREP2,3 was cut with Hind III and Sst I, and the fragment comprising REP2, REP3 and ori sequences was gel-purified and joined to the linearized pICPOT*. The resultant plasmid, comprising REP2 REP3, ori, POT1 and amp$^r$ sequences, was designated pMPOT1. REP1 was then removed from pICREP1 as a Bgl II-Nar I fragment and was ligated to pMPOT1, which had been cleaved with Bgl II and Nar I. The product of this ligation was designated pMPOT2 (deposited with ATCC as a *S. cerevisiae* strain Δtpi29 transformant, accession number 20744).

B. Insertion of VSB Expression Unit into pMPOT2.

Plasmid pVSB was digested with Cla I and Bam HI, and the 2.2 kb fragment containing the B-chain expression unit was purified by agarose gel electrophoresis and EtOH precipitation. Plasmid pMPOT2 was also digested with Cla I and Bam HI. The fragments were ligated overnight at room temperature in the presence of T4 DNA ligase and the reaction mixture used to transform *E. coli* HB101 to ampicillin resistance. DNA was prepared from transformants and the presence of the insert was verified by digestion with Cla I and Bam HI followed by agarose gel electrophoresis of the digested DNA. The resulting expression vector was designated pVSBm (FIG. 7).

C. Insertion of the pA7 Expression Unit into pMPOT2

Plasmid pA7 was digested with Cla I and Bam HI, and the 2.2 kb fragment containing the A-chain expression unit was isolated by agarose gel electrophoresis. Plasmid pMPOT2 was digested with Cla I and Bam HI, and the linear vector fragment was isolated by agarose gel electrophoresis. The fragments were ligated and the resultant plasmid termed pA7m.

D. Transformation of pVSBm and pA7m into Yeast Host Cells

Plasmids pVSBm and pA7m were used to transform *S. cerevisiae* strain E18 #9 by conventional methods. Strain E18 #9 is a diploid produced by crossing strains E11-3c (ATCC No. 20727 leu2-3,112 Δtpil::LEU2 pep4-3 MATα) and Δtpi29 (Δtpil::LEU2 pep4-3 leu2-3,112 MATa his4-580). Δtpi29 was produced by disrupting the TPI1 gene of strain E2-7b (ATCC No. 20689), essentially as described by Rothstein (*Meth. in Enzymology* 101:202-210, 1983). Transformants were grown at 30° C. in rich medium containing glucose.

EXAMPLE IV

Purification of AA Isoform and BB Isoform Protein from Yeast

The AA isoform and the BB isoform were purified from yeast culture supernatants. Strain E18 #9 transformed with either pA7m or pVSBm was pelleted to remove the yeast cells and the supernatant was harvested. The supernatant broth was concentrated using Millipore Pellicon Cassettes (Millipore, Bedford, MA).

The concentrates were pelleted by centrifugation in a Beckman J-6B centrifuge (Beckman Instruments, Inc., Brea, CA.) at 4200 rpm for 30 minutes to remove the turbidity. EDTA was added to a final concentration of 10 mM and the pH of the mixture was adjusted to pH 5.5 with 5M NaOH. The concentrate was then diluted with water to conductivity of about 10 millimhos.

The resultant concentrate was chromatographed on an S-Sepharose Fast Flow (Pharmacia, Piscataway, N.J.) column. The column was washed with 20 mM sodium phosphate, 0.1M sodium chloride, pH 7.3. The column was then eluted with 20 mM sodium phosphate, 1 M sodium chloride, pH 7.3. The absorbance at 280 nm of the eluate was followed and the peak fractions were collected and pooled.

The eluate was frozen at −20° C. and then thawed. The particulate material was removed from the eluate by centrifugation. The supernatant was harvested and the pH adjusted to 3.0 with 0.87M acetic acid. The eluate was concentrated using an Amicon YM10 filter (Amicon, Danvers, MA). The concentrated eluate was diluted with five volumes of 1M acetic acid to lower the sodium chloride concentration to about 0.2M.

The eluate was then chromatographed on a second S-Sepharose column (Pharmacia, Piscataway, N.J.). The column was washed with 1M acetic acid and the absorbance at 280 nm of the eluate was followed until it returned to baseline. The column was eluted with 1M acetic acid, 1.5M ammonium chloride, pH 4.8–5.0. The $A_{280}$ of the eluate was followed and the PDGF isoform was harvested as the last $A_{280}$ peak. The peak fractions were pooled and concentrated using an Amicon YM10 filter.

The concentrated eluate was then applied to a Sephadex G-50 Superfine (Pharmacia, Piscataway, N.J.) column. The sample volume was about 1% of the column volume. The column was run at a flow rate of 5 cm/hr in 1M ammonium acetate pH 9.0. The purest fractions, as determined by SDS-gel electrophoresis, were pooled and the pH adjusted to 4.0 with acetic acid.

The concentration of PDGF isoform was determined by amino acid composition analysis using the Pico-Tag method of Waters Associates (Milford, MA)(Bidlingmeyer et al., *J. Chromatography* 336:93–104, 1984). Briefly, protein samples were hydrolyzed in the vapors of constant boiling HCl (Pierce Chemical Co., Rockford, IL) containing 1% (V/V) phenol for 22–24 hours, in vacuo, at 110° C. The amino acids were then derivatized with phenylisothiocyanate (PITC) and the resulting phenylthiocarbamyl amino acids were separated by reverse phase HPLC using a Varian 5500 (Varian, Palo Alto, CA) and recorded on a Varian Vista 400 data system.

The PDGF isoforms isolated in this manner were used for immunization, radio labeling and as ELISA assay antigen.

EXAMPLE V

Preparation of PDGF Monoclonal Antibodies

A. Immunization of Mice

Eight-week-old female Balb/c mice were immunized with purified BB isoform or AA isoform as described below. 500 ng BB isoform was blotted onto nitrocellulose paper (Schleicher & Schuell, Keene, NH) and dried at 37° C. for one hour. The nitrocellulose paper was then implanted into the peritoneal cavity of the Balb/c mice. The mice were then injected with 200 ul of Freund's Adjuvant (ICN Biochemicals, Costa Mesa, CA). This procedure was repeated a total of four times at two-week intervals. Four days prior to the fusion date, the mice were intravenously injected with 100 ng BB isoform.

Immunization of Balb/c mice with purified AA isoform was done essentially as described for the BB isoform mouse immunizations. Briefly, between 1 and 2 ug. of pure AA isoform, purified as described in Example IV, was blotted onto nitrocellulose paper and dried at 37° C. for one hour. The nitrocellulose paper was implanted into the peritoneal cavity of eight-week-old Balb/c mice. The mice were then injected with 200 ul Freund's Adjuvant. This procedure was repeated four times at two-week intervals. Four days prior to the fusion date, the mice were intravenously injected with 100 ng AA isoform.

B. preparation of Immunized Mouse Spleen and Lymph Node Cells

To prepare for the fusion between the immunized mouse cells and the mouse myeloma cell line, the spleens and lymph nodes of the immunized mice were removed and minced with scissors on top of fine-mesh stainless steel screens. The minced tissues were washed through the fine screens into petri dishes with 10 ml RPMI 1640 (RPMI, GIBCO, Lawrence, MA). The remainder of the minced tissues was pressed through the screens with a spatula and the screens were washed with 5 ml RpMI. To remove any remaining cell material, the bottoms of the screens were scraped and the cell material was added to the petri dishes.

The strained tissues were transferred to 50 ml centrifuge tubes. The petri dishes were washed with 10 ml RPMI to remove any remaining material. The cell suspensions were centrifuged for 10 minutes at 200×g. The supernatants were discarded and the pellets were resuspended in 4 ml RPMI. After resuspension, 1 ml fetal calf serum (BioCell, Carson, CA) was added to each tube.

The red blood cell contaminants were lysed by adding 18 ml sterile distilled water to the cell suspensions. The mixtures were swirled quickly and 5 ml 4.25% NaCl was added to each tube. The cell suspensions were centrifuged for 10 minutes at 200×g. The supernatants were discarded and the cell pellets resuspended in 10 ml RPMI.

To remove any remaining tissue material, the suspensions were filtered through two layers of sterile gauze into 50 ml tubes. The centrifuge tubes and gauze were rinsed with an additional 10 ml RPMI. Dilutions of the resultant cell suspensions were counted with a hemacytometer to determine the yield of lymphocytes. The prepared cells were kept at room temperature for approximately one hour until ready for use.

C. Preparation of Mouse Myeloma Cells

The NS-1 mouse myeloma cell line was used for the fusion. To optimize the fusion procedure, the NS-1 line was cloned out to isolate a clone with a high fusion efficiency. The NS-1 cells were cloned out by limiting dilution into 96-well microtiter plates at an average of five and ten cells per well in NS-1 medium (Table 3)+$2.5\times10^6$ thymocytes/ml (as prepared in Example V.D., below). The plates were incubated at 37° C., 7% $CO_2$ for ten days.

TABLE 3

NS-1 Medium
  For a 500 ml solution:
  5 ml 10 mM non-essential amino acids (Gibco, Lawrence, MA)
  5 ml 100 mM sodium pyruvate (Irvine, Santa Ana, CA)
  5 ml 200 mM L-glutamine (Gibco)
  5 ml 100x Penicillin/Streptomycin/Neomycin (Gibco)
  75 ml inactivated fetal calf serum (BioCell, Carson, CA)
  1 gm $NaHCO_3$
  Add RPMI 1640 (Gibco, Lawrence, MA) to a total volume of 500 ml.
  Sterilize by filtration through a 0.22 um filter.

Table 3 continued
100×HT Stock
  38.5 mg thymidine
  136.10 mg hypoxanthine (Sigma, St. Louis, MO)
  Dissolve the thymidine and hypoxanthine in distilled $H_2O$ and bring volume up to 100 ml. Warm the solution to 60°-70° C. to dissolve the solids. After the solids have dissolved, readjust the volume to 100 ml. Sterilize by filtration through a 0.22 um filter. Store frozen at −20° C.
1000×A Stock
  17.6 ng aminopterin
  Add sterile distilled water to the aminopterin and bring the volume to 50 ml. Add 1N NaOH drop-wise until the aminopterin dissolves. Bring the final volume to 100 ml with distilled $H_2O$. Sterilize by filtration through a 0.22 um filter. Store frozen at −20° C.
50×HAT
  50 ml 100×HT
  5 ml 1000×A stock
  45 ml distilled $H_2O$
  Sterilize the solution by filtration through a 0.22 um filter. Store frozen at −20° C.

Table 3 continued
Freezing Medium
  7 ml NS-1 medium
  2 ml fetal calf serum
  1 ml DMSO
  Mix the ingredients and make fresh for each freezing.

On day ten, the cells were examined microscopically and screened for wells containing single colonies. On the same day, 100 ul of fresh NS-1 medium containing $2.5\times10^6$ thymocytes/ml was added to each well. On the fourteenth day eight of the most vigorously growing single colonies were chosen to expand for fusion.

The eight candidate colonies were transferred to individual 24-well plates containing 1.5-2 ml NS-1 medium+$2.5\times10^6$ thymocytes/well. These plates were maintained at 37° C., 7% $CO_2$ and the cells split at appropriate intervals by expanding the cells to fresh wells of the plate and adding fresh NS-1 medium. This procedure was repeated until there was a sufficient number of cells to expand into a 75 cm2 tissue culture flask. At this point, $1\times10^7$ cells from the growing cultures were used to inoculate a 75 cm² tissue culture flask containing 50 ml NS-1 medium. The flasks were incubated at 37° C., 7% $CO_2$, until the cells reached a density of at least $5\times10^5$ cells/ml. The cells were then harvested by centrifugation and diluted to a concentration of approximately $5\times10^6$ cells/ml with freezing medium (Table 3). The cells were divided into 1 ml aliquots and frozen stepwise first at −80° C. and then at −130° C.

To assay the clones of NS-1 cells for fusion efficiency, one vial for each clone was quickly thawed in water held at 37° C. The cells were inoculated into flasks containing NS-1 medium to a concentration of $2\times10^5$ cells/m1. The cells were grown at 37° C. with 7% $CO_2$. The cells were cut back to $2\times10^5$ cells/ml daily. One day before the fusion, two 75 cm² flasks containing 50 ml of cell culture were set up. Each of the candidate NS-1 clones was mixed with immunized mouse spleen cells and fused as described in Example V.E., below.

The results of the fusions showed that one of the single-colony isolates showed an increased fusion efficiency. This clone was designated clone F and was subsequently used as the myeloma cell line in all further fusions.

D. Preparation of Thymocytes

Thymus glands obtained from baby mice were the source of the thymocytes which were used as a feeder layer to condition the culture media for the cell fusions. Thymus glands were obtained from three- to four-week-old Balb/c mice. The thymus glands were rinsed with NS-1 medium and minced on a fine-mesh stainless steel screen with scissors. The minced tissues were rinsed through the screen with 10 ml NS-1 medium into a petri dish. The thymus tissue was then pressed through the screen with a spatula into the petri dish. The screen was then washed with 10 ml NS-1 medium. The bottom of the screen was scraped to remove any adhered tissue and the tissue was pooled in the petri dish. The strained tissue was transferred to a 50 ml centrifuge tube through two layers of sterile gauze. The petri dish and gauze were rinsed with an additional 10 ml NS-1 medium. The cells were centrifuged for 10 minutes at 200×g. The supernatants were discarded and the pellets resuspended in 10 ml NS-1 medium. Dilutions of the cell suspensions were counted using a hemacytometer. The yield from two thymus glands was routinely about 400 million cells. The cells were stored at room temperature until ready for use.

E. Fusion of Immunized Mouse Cells with NS-1 Cells

To prepare cells for fusion, the NS-1 clone F cells, grown as described above, were transferred to 50 ml centrifuge tubes and centrifuged for 10 min at 200×g. The supernatants were discarded and the cell pellets were resuspended and combined in 10 ml RPMI. The cell suspension was counted with a hemacytometer to monitor the cell viability as determined by trypan blue exclusion. The cell viability was determined to be greater than 95%.

For fusion, $2.5 \times 10^7$ NS-1 clone F cells were added to the prepared immunized mouse cells (prepared as described above). The mixed cells were centrifuged for 10 minutes at $200 \times g$. The supernatant was removed by aspiration with a pasteur pipet attached to a vacuum line. The cell pellet was resuspended in 100 ul RPMI and warmed in a water bath at 37° C.

A 1 ml 50% polyethylene glycol (PEG) solution (1,500 mw), which was made up in RPMI, was pH adjusted within the range of pH 7.0 to pH 8.0 with 20 ul 1% sodium bicarbonate. The PEG was added to the cell suspension over a period of one minute with gentle stirring. The suspension was stirred for an additional minute. Two ml of NS-1 medium was added over a period of 2 minute with gentle stirring. Eight ml NS-1 medium was added over a period of 2 minutes. The suspension was centrifuged at $125 \times g$ at room temperature for 10 minutes. The supernatant was discarded and 25 ml NS-1 medium was added to gently resuspend the pellet. The cells were harvested gently into a pipet and transferred to a 175 cm$^2$ flask.

Four hundred million thymocytes (prepared as above) were added to the flask. The volume was adjusted to 160 ml with NS-1 medium and the mixture was incubated at 37° C., 7% $CO_2$ for two to four hours.

After incubation, 3.2 ml of $50 \times$ HAT (Table 3) was added. The cell suspension was transferred to eight 96-well culture plates at 200 ul per well, using pipet tips with the ends cut off to avoid shearing forces. The plates were incubated at 37° C. in a humid incubator with 7% $CO_2$. The plates were examined microscopically after three days to determine fusion efficiency with the expectation of approximately 5 hybridoma colonies per well. The cells were fed after seven days by replacing 100 ul of the medium with fresh NS-1 medium containing 1 x HAT and $2.5 \times 10^6$ thymocytes per ml. The hybridomas were tested between days 9 and 14 for the production of specific antibodies. Select hybridomas from fusions numbers 120, 121 and 127 were chosen for further characterization. Hybridomas from fusions 120 and 121 were derived from BB immunized mice, hybridomas from fusion 127 were derived from AA-immunized mice.

EXAMPLE VI

Identification of the Antibodies Produced by Fusions 120 and 121

Hybridomas from cell fusions 120 and 121 were tested for the production of antibodies to the B-chain of PDGF. Assays used for identification of positive hybridomas included enzyme linked immunosorbent assays (ELISA), radioimmunoprecipitation (RIP) assays, and Western blots.

A. Screening fusions 120 and 121 by ELISA

The ELISA assays were carried out in 96-well microtiter plates which had been coated with B-chain protein. The microtiter plates used for assaying fusion 20 were coated with 200 ng/ml BB isoform and those used for assaying fusion 121 were coated with 500 ng/ml BB isoform. To coat the wells, BB isoform was diluted to the appropriate concentration (200 ng/ml or 500 ng/ml) in ELISA buffer A (Table 4) and 50 ul of the BB isoform solution was added to each well. The plates were incubated for 1.5 hour at 37° C. After the incubation, the plates were washed twice with ELISA buffer C (Table 4). The plates were then incubated with 150 ul/well of ELISA Buffer B (Table 4) for two hours at 37° C. The buffer was then removed by two washes with ELISA buffer C. These plates were stored dry, overnight at 4° C.

TABLE 4

ELISA Buffer A
 0.1M $Na_2HCO_3$, pH 9.6
 0.02% $NaN_3$
ELISA Buffer B
 This buffer may be made with 1% or 2% bovine serum albumin (BSA, Sigma, St. Louis, MO)
 5 or 10 g BSA (for 1% or 2% BSA, respectively)
 250 ul Tween 20 (Sigma, St. Louis, MO)
 100 mg $NaN_3$
 Add phosphate-buffered saline pH 7.2 (PBS, Sigma St. Louis, MO) to a final volume of 500 ml. Alternatively, the buffer may be made up as 1% or 2% BSA in ELISA Buffer C.
ELISA Buffer C
 500 ul Tween 20 (Sigma)
 200 mg $NaN_3$
 Add PBS to a final volume of 1 liter.

Table 4 continued

ELISA Buffer D
 48 ml Diethanolamine (Sigma)
 352 ml distilled $H_2O$
 24.5 mg $MgCl_2$
 Adjust the pH of the solution to 9.8 with HCl. Add distilled water to a final volume of 500 ml. Store in the dark or in a bottle wrapped in foil.
RIP Buffer
 20 mM Tris-base
 100 mM NaCl
 1 mM $Na_2$EDTA
 0.5% NP-40
 0.5% sodium deoxycholate
 10 mM NaI
 1% BSA
 Adjust the pH to 8 with concentrated HCl.
TNEN
 20 mM Tris-base
 100 mM NaCl
 1 mM $Na_2$EDTA
 0.5% NP40
 Adjust the pH to 8 with concentrated HCl.

The ELISA assay was carried out on microtiter plates, prepared as described above, which had been warmed to 37° C. Fifty ul hybridoma culture supernatant was added to each test well. The plates were incubated for one hour at 37° C. After incubation, the plates were washed two times with ELISA Buffer C. The wells were then incubated for one hour at 37° C. with 50 ul of alkaline phosphatase-conjugated rabbit anti-mouse IgG (Sigma, St. Louis, MO). The wells were then washed three times with ELISA buffer C. After the wash step 50 ul of substrate, containing 30 mg p-nitrophenyl phosphatase (Sigma, St. Louis, MO)+50 ml ELISA buffer D, was added to each well and the plates were incubated for one hour at 37° C. The plates were then scored using a Dynatech ELISA plate reader (Dynatech Laboratories, Inc. Alexandria, VA) using a filter to monitor absorbance at 405 nm. Those wells with $A_{405}$ readings of greater than or equal to 0.05 were taken as positives.

The positive candidates were re-assayed by ELISA assay as described above. These samples were assayed in duplicate with microtiter plates coated with 500 ng/ml BB isoform or which had been incubated with ELISA buffer A alone. Positive results shown by the candidates on the latter plates (coated with buffer A alone) indicated nonspecific binding to plastic. Candidates which showed $A_{405}$ greater that 0.09 on ELISA plates coated with BB isoform and no reaction against the plastic were chosen for further analysis. The latter group of candidates included hybridomas from fusion 120 in well number 2 of plate number 1, termed 120.1.2, and hybridomas from fusion 121 in well number 1 of plate number 6, termed 121.6.1.

B. Screening Hybridomas by Radioimmunoprecipitation (RIP) Assay

Radioimmunoprecipitation assays were done on hybridoma culture supernatants determined positive by ELISA. Three million cpm of $^{125}$I-labeled BB isoform (labeled with $^{125}$I using an Amersham Bolton/Hunter kit) was preadsorbed to 50 ul *Staphylococcus aureus* stock solution (Sigma, St. Louis, MO) to rid the assay of nonspecific binding. The mixture was incubated 30 min on ice and pelleted to remove any nonspecifically bound BB isoform. The supernatant, comprising the $^{125}$I-labeled BB isoform, was transferred to a fresh tube.

The assays were carried out in 12×75 mm tubes to which was added 50 ul of hybridoma culture supernatant and 100 ul $^{125}$I-BB (100,000 cpm/ml) isoform diluted in RIP buffer (Table 4). The tubes were incubated at room temperature for two hours. After incubation, 30 ul rabbit anti-mouse IgG (Cappel Laboratories, Malvern, PA), diluted 1:10 in RIP buffer, was added to each tube. The tubes were incubated for an additional two hours, after which 1 ml *S. aureus,* diluted 1:50 in RIP buffer, was added to each tube. The tubes were incubated for 45 minutes at room temperature before the *S. aureus* was pelleted by centrifugation. The supernatants were discarded and the pellets washed twice, once in RIP buffer, once in TNEN (Table 4). The *S. aureus* was pelleted by centrifugation and the supernatants were discarded. The pellets were resuspended in 100 ul RIP buffer and counted in a Beckman gamma counter (Beckman Instruments Inc., Brea, CA) to monitor the cpm of $^{125}$I-BB isoform precipitated. Candidates that were shown to be positive through both ELISA and RIP screens included hybridomas 120.1.2 and 121.6.1.

C. Cloning of Hybridomas

Hybridomas 120.1.2 and 121.6.1 were cloned twice by limiting dilution and screened by ELISA to isolate and assure the monoclonality of the hybridomas. The cloning by limiting dilution plating was carried out as follows. The parental wells, well number 2 of plate number 1 for fusion 120 and well number 1 of plate number 6 for fusion 121, were diluted with NS-1 medium to a concentration of 25 cells per ml of culture medium. The cell mixtures were then plated into 96-well culture plates at 200 ul per well, averaging approximately .5 hybridoma cells per well. Thymocytes (2×10⁵ cells/well) were included in the culture medium to help condition the growth medium for the hybridomas. After seven days in culture the wells were individually scanned microscopically to screen for wells containing single colonies of cells.

Those wells containing single colonies were assayed by ELISA or RIP, using BB isoform as the antigen, for the presence of specific antibodies in the conditioned media.

Cells positive for antibody production were expanded in culture to obtain large amounts of the monoclonal antibodies. Cells found to be positive for antibody production following the first round of cloning included 120.1.2.1 and 121.6.1.1, the last digit indicating the clone number of the single colony isolated in the first cloning. One clone obtained for each of the hybridomas was then subjected to a second round of cloning by limiting dilution, using conditions identical to those described above. The resultant clones included clones termed 120.1.2.1.2 and 121.6.1.1.1; the last digit of these clones indicates the clone number from the second round of deposited with American Type Culture Collection, Rockville, MD. (ATCC Accession Nos. HB 9610 and HB 9613", respectively).

EXAMPLE VII

Identification of the Antibodies Produced by Fusion 127

The hybridomas from fusion 127 were screened for the production of antibodies specific for AA isoform using the RIP assay.

Purified AA isoform (described in Example IV) was labeled with $^{125}$I as follows. Three ug of pure AA isoform was added to a 12×75 mm tube. To this protein was added 150 ul PBS, 3 mCi of $^{125}$I (Amersham Corporation, Arlington Heights, IL) and 1 Iodobead (Pierce Chemical Co, Rockford, IL) and the mixture was incubated for 15 minutes on ice.

The unincorporated $^{125}$I was removed by gel filtration of the sample over a 10 ml G-25 Sephadex (Pharmacia) column which had been equilibrated with 10 mM acetic acid containing 0.25% gelatin (equilibration buffer). The sample was applied to the column and the column was washed with equilibration buffer. One ml fractions were collected and 1:100 dilutions of the fractions were counted on a Beckman gamma counter to determine the peak of $^{125}$I-labeled protein that was eluted. The peak fractions were pooled and stored at 4° C. until used.

For the initial screening, pools of culture supernatants were assayed by RIP essentially as described in Example VI.B. Twenty-five ul aliquots of cell-culture conditioned medium from 4 independent wells were pooled and then placed into the wells of a 96-well V-bottom microtiter plate resulting in a final volume of 100 ul for the assay. To each well, 20 ul of $^{125}$I labeled AA isoform (5×10⁴ cpm/well diluted in RIP buffer) was added. The plates were incubated for two hours at room temperature. After incubation, 10 ul of a 1 mg/ml affinity purified rabbit anti-mouse IgG stock (Cappel Laboratories, Malvern, PA) was added to each well and the plates were incubated for 1.25 hr at room temperature. Twenty ul of a 10% *Staphylococcus aureus* stock solution was added to each well and incubated for fifteen minutes at room temperature. The *S. aureus* was pelleted by centrifugation at 1,200×g for five minutes. The supernatants were removed by aspiration and the pellets were washed with 100 ul RIP buffer. The *S. aureus* was pelleted by centrifugation and the supernatants were removed as described above. The pellets were then resuspended in 100 ul of RIP buffer, transferred to test tubes, and the tubes counted in a Beckman gamma counter to monitor the cpm of $^{125}$I-AA isoform precipitated. All potential positive candidates were reassayed without pooling using the RIP assay as described above.

Candidates found to be positive after this screening procedure included well number 7 from plate 5, termed 127.5.7, and well number 2 from plate number 8, termed 127.8.2. These candidates were cloned by limiting dilution and screened by ELISA assay essentially as described in Example VI.C. using AA isoform as the coating antigen. Positive clones after the first cloning step included 127.5.7.3 and 127.8.2.2 (the final digit indicating the well number of the cloning plate). Positive clones after the second cloning step included 127.5.7.3.1 and 127.8.2.2.2 (the final digit indicating the well number of the cloning plate). Hybridomas 127.5.7.3.1 and 127.8.2.2.2 have been deposited with American Type Culture Collection, Rockville, MD. (ATCC Accession Nos. HB 9612 and HB 9611", respectively).

EXAMPLE VIII

Characterization of Monoclonal Antibodies 120.1.2.1.2, 121.6.1.1.1, 127.5.7.3.1 and 127.8.2.2.2

A. Western Transfer Assay

Candidates 120.1.2.1.2, 121.6.1.1.1, 127.5.7.3.1 and 127.8.2.2.2 were tested for the ability to bind AA, AB and/or BB isoforms of PDGF by Western blot, essentially as described by Towbin et al. (*Proc. Nat'l. Acad. Sci. USA* 76:4350–4354, 1979) and Gordon et al. (U.S. Pat. No. 4,452,901). Briefly, about 250 ng of each isoform was electrophoresed in a 15% sodium dodecyl sulfate polyacrylamide gel under non-reducing conditions. The proteins were electrophoretically transferred to nitrocellulose paper using conditions described by Towbin et al. (ibid.). Conditioned media from the positive candidates were added to envelop the nitrocellulose blots and the blots were incubated to allow binding of antibody to the protein. Following removal of the conditioned media, biotin-conjugated horse anti-mouse antibody (Vector Laboratories, Burlingame, CA) was added to the blots under conditions which allow antibody binding. Excess antibody was removed and the blots were developed by incubation with the Vector ABC kit (Vector Laboratories), under conditions suggested by the manufacturer, followed by addition of horseradish peroxidase substrate (Bio Rad, Richmond, CA). A summary of the results for antibody detection of the PDGF isoforms by western blot is presented in Table 5.

TABLE 5

| Antibody | AA | AB | BB |
|---|---|---|---|
| 120.1.2.1.2 | − | − | + |
| 121.6.1.1.1 | − | + | + |
| 127.5.7.3.1 | + | + | − |
| 127.8.2.2.2 | + | − | − |

(+) indicates binding
(−) indicates no binding

B. Neutralization Assays

Characterization of the monoclonal antibodies also included neutralization assays. Purified antibodies from the four anti-PDGF antibody-producing hybridomas, 120.1.2.1.2, 121.6.1.1.1, 127.5.7.3. and 127.8.2.2.2, were assayed for the ability to neutralize the three isoforms of PDGF. Two different neutralization assays were conducted.

The assays utilized $^{125}$I-labeled PDGF isoforms. The method for labeling the AA and BB isoforms has been described in Examples VII and VI.8, respectively. To label the AB isoform, 3 ug of pure AB isoform (isolated from platelet lysates by sequential affinity chromatography on an antibody 120.1.2.1.2 column, followed by an antibody 121.6.1.1.1 column as described in Example X.) was added to 150 ul of PBS, 3 mCi of $^{125}$I (Amersham Corp., Arlington Heights, IL) and 1 iodobead (Pierce Chemical Co., Rockford, IL). The mixture was incubated for thirty minutes on ice. Unincorporated $^{125}$I was removed by gel filtration of the sample over a 10 ml G-25 Sephadex column which had been equilibrated with 10 mM acetic acid containing 0.25% gelatin. The sample was applied to the column, then the column was washed with the same buffer. One ml fractions were collected and 1:100 dilutions of the fractions were counted on a Beckman gamma counter to determine the peak of $^{125}$I-labeled protein. The peak fractions were pooled and stored at 4° C. until used.

For the first neutralization assay, 5 ug of purified antibody was incubated with approximately 2 ng $^{125}$I-labeled ligand ($^{125}$I-AA, $^{125}$I-BB or $^{125}$I-AB) in a total volume of 100 ul of binding medium (Ham's medium F-12 [Gibco] buffered at pH 7.4 with 25 mM HEPES and supplemented with 0.25% BSA) for one hour at 37° C. The solution was diluted to 3.2 ml with binding medium and then added to triplicate wells of monolayers of human dermal fibroblasts, cultured in 24-well culture plates to a density of approximately 40,000 cells per well. The antibody/ligand mixture was incubated with the cells for three hours at 4° C. The cells were then washed three times with pBS, pH 7.2. The total amount of $^{125}$I-labeled ligand bound to the test cells was determined by extracting the cells with PBS containing 1% Triton X-100 Sigma, St. Louis, MO). The detergent extract was removed from the wells and counted in a Beckman gamma counter. The ability of an antibody to neutralize ligand binding is demonstrated by a decrease in the amount of $^{125}$I-ligand bound to the monolayer of dermal fibroblasts.

Antibody neutralization of ligand binding was also determined using a modification of the radioreceptor assay (Bowen-Pope and Ross, *J. Biol. Chem.* 257:5161, 1982). Briefly, five ug of pure antibody was incubated with 1 ng of pure unlabeled ligand (AA, BB or AB) for one hour at 37° C. in a total volume of 100 ul of binding medium. The sample was diluted to 3.2 ml with binding medium, then added to triplicate wells of monolayers of human dermal fibroblasts (grown as described above) and incubated for 3 hours at 4° C. The cells were washed three times with PBS and subsequently incubated with 1 ng/ml of $^{125}$I-AB for two hours at 4° C. The cells were washed three times with PBS to remove unbound $^{125}$I-AB and extracted with 1% Triton X-100. The extract was counted in a Beckman gamma counter to determine the amount of $^{125}$I-AB bound. The ability of the antibody to neutralize ligand binding in this assay was detected by an increase in $^{125}$I-AB binding.

A summary of the antibody neutralization data obtained from the two assays is presented in Table 6.

TABLE 6

| Antibody | Ligand | | |
|---|---|---|---|
| | AA | AB | BB |
| 120.1.2.1.2 | − | − | − |
| 121.6.1.1.1 | − | + | + |
| 127.5.7.3.1 | + | + | − |
| 127.8.2.2.2 | + | − | − |

(+) indicates positive for neutralization of ligand binding
(−) indicates negative for neutralization of ligand binding

C. Radioimmunoprecipitation (RIP) Assay

The four monoclonal antibodies, 120.1.2.1.2, 121.6.1.1.1, 127.5.7.3.1 and 127.8.2.2.2, were screened for the ability to immunoprecipitate each of the $^{125}$I-labeled isoforms of PDGF. The assays were done essentially as previously described (see example VI.B.). Briefly, either 50 ul of conditioned culture medium or 2 ug of purified antibody diluted in 50 ul of RIP buffer (Table 4) was incubated with approximately 100,000 counts per minute of each of the $^{125}$I-labeled PDGF isoforms. The immune complexes were precipitated by the addition of rabbit anti-mouse IgG antibody and S. aureus. The S. aureus pellets were washed twice with 1 ml RIP buffer, transferred to a new tube and counted in a gamma counter to determine the amount of $^{125}$I-labeled isoform precipitated. NS-1 medium alone was used as a negative control to monitor the level of nonspecific binding by the labeled isoforms to the S. aureus. The results are presented in Table 7. The nonspecific cpm precipitated in the presence of NS-1 medium alone have been subtracted from the data shown.

TABLE 7

| Immunoprecipitation of $^{125}$I-labeled Isoforms of PDGF CPM Precipitated | | | |
|---|---|---|---|
| Antibody | $^{125}$I-AA | $^{125}$I-AB | $^{125}$I-BB |
| 120.1.2.1.2 | 0 | ND | 13,269 |
| 121.6.1.1.1 | 339 | 4,426 | 7,010 |
| 127.5.7.3.1 | 7,847 | 1,491 | 8 |
| 127.8.2.2.2 | 8,636 | 188 | 172 |

ND: Not determined

D. Immunoglobulin Subclass Determination

Immunoglobulin subclass determinations of the monoclonal antibodies were made using an ELISA assay. Purified BB isoform was used as antigen for monoclonal antibodies 120.1.2.1.2 and 121.6.1.1.1. Purified AA isoform was used as the antigen for monoclonal antibodies 127.5.7.3.1 and 127.8.2.2.2. The ELISA assay was carried out as follows. The wells were coated with 100 ul/well of 200 ng/ml antigen diluted in ELISA buffer A (Table 4). The wells were incubated for two hours at 37° C. After incubation, excess antigen was removed and the wells were washed two times with ELISA buffer C (Table 4). The plates were then incubated with 150 ul/well of ELISA buffer B (Table 4) for two hours at 37° C. The buffer was removed by two washes with ELISA buffer C. One hundred ul of a lug/ml solution of purified antibody (Example IX) diluted in ELISA buffer B was then added to each well and the wells were incubated for one hour at 37° C. The unbound antibody was removed by three washes with ELISA buffer C. Rabbit anti-mouse subclass-specific antibodies (Miles Scientific, Naperville, IL.) were then added. One hundred ul of a 1 ug/ml solution of rabbit anti-mouse subclass specific antibody (specific for IgG, IgG$_1$, IgG$_{2a}$, IgG$_{2b}$, IgG$_3$, or IgM) was added to each well and the wells were incubated for one hour at 37° C. The rabbit anti-mouse antibody was removed by three washes with ELISA buffer C. One hundred ul of alkaline phosphatase-conjugated goat anti-rabbit antibody (1 ug/ml) was then added to each well. The wells were incubated for one hour at 37° C. The conjugate was removed by three washes with ELISA buffer C. Fifty ul substrate reagent (30 mg p-nitrophenyl phosphatase (Sigma, St. Louis, Mo.) +50 ml ELISA buffer D (Table 4)) was added and the wells were incubated at 37° C. The wells were then read for color development at 405 nm using a Dynatech ELISA plate reader (Dynatech Laboratories, Alexandria, VA.). The subclass determinations made using this assay method were 120 1 2.1.2 (IgG$_1$), 121.6.1.1.1 (IgG$_1$), 127.5.7.3.1 (IgG$_1$) and 127.8.2.2.2 (IgG$_{2b}$).

EXAMPLE IX

Large Scale Culture of Hybridomas

Following identification and characterization of the antibodies, the hybridomas were cultured for the production of large quantities of antibodies. This large scale production of antibodies was carried out by culturing the hybridomas in ascites as described below.

Balb/c mice were injected intraperitoneally with 1 ml of Pristane (2,6,10,14-tetramethylpentadecane, Aldrich Chemical, Milwaukee, WI) between seven and ten days before being injected with the hybridomas. The mice were injected intraperitoneally with approximately $5 \times 10^6$ cells per mouse.

Ascites fluid was removed from the mice with an 18 gauge needle between seven and ten days after injection. Any cells and/or cell material were removed from the ascites fluid by centrifugation.

Antibodies were purified from ascites fluid using a protein A-Sepharose CL-4B (Sigma, St. Louis, MO) column equilibrated with TNEN (Table 4). The ascites fluid was mixed with an equal volume of TNEN buffer. The solution containing the ascites was then applied to the column and cycled over the column two times. The column was washed with 3–4 column volumes of TNEN and bound material was eluted with 0.1M sodium citrate, pH 3.0. Fractions were collected, neutralized by the addition of 1.5M Tris-base, pH 8.5, and the absorption at 280 nm was monitored. Peak fractions were pooled and the protein concentration was determined by adsorption at 280 nm using an extinction coefficient of 1.4 for a 1 mg/m solution.

EXAMPLE X

Purification of Specific PDGF Isoforms

The monoclonal antibodies described in the present invention, immobilized on solid matrices, were used in combination to isolate specific isoforms of PDGF from complex protein mixtures. Sources of PDGF include outdated platelets and transformed yeast culture media.

A. Preparation of Platelet Lysates

PDGF was purified from outdated platelet preparations which were obtained from regional blood banks. The platelets were frozen and thawed three times to disrupt the platelets. The platelets were heated to 57° C. for 60 minutes. The platelet debris was removed from the sample by centrifugation. After centrifugation, the supernatant was decanted and adjusted to a pH of 7.4 with 1M Tris-base. The sample was loaded onto a CM-Sephadex column (Pharmacia, Piscataway, NJ) and the column was washed with 0.01M Tris pH 7.4, 0.19M NaCl, then eluted with 0.01M Tris pH 7.4, 0.5M NaCl. The peak eluate fractions containing PDGF activity, as determined by radioreceptor assay (as described below), were pooled and concentrated on an Amicon concentrator using a PM-10 membrane (Amicon, Danvers, MA). The sample was then frozen at −80° C.

B. Radioreceptor Assay

The radioreceptor assay for PDGF (Bowen-Pope and Ross, *J. Biol. Chem.* 257: 5161, 1982) is a specific and sensitive (0.2-2 ng/ml PDGF) method for detecting biologically active PDGF-like material. In this assay, PDGF-like material was tested for its ability to compete with purified, radio-labeled $^{125}$I-AB isoform for binding sites on cell surface PDGF receptors. Results were interpreted by comparison to a standard curve generated with purified, unlabeled AB isoform. Comparison of results obtained with other assay methods (e.g., ELISA) provided an indication of the strength of the receptor/ligand interaction in addition to quantitation of the material bound. The assay was conducted as follows Subconfluent monolayers of diploid human fibroblasts were prepared by plating $1.5 \times 10^4$ cells per well in 24 well cluster trays in Dulbecco's Modified Eagles Medium (DMEM) supplemented with 1% fetal calf serum. Cultures were set on an ice tray and rinsed once with ice-cold binding medium (Ham's medium F-12 buffered at pH 7.4 with 25 mM HEpES and supplemented with 0.25% BSA). One ml/well of test substance in binding medium was added and the cultures were incubated at 4° C. on a platform rocker for 3-4 hours. The trays were then placed on ice, aspirated, rinsed once with cold binding medium and incubated for one hour as above with 1 ml/well binding medium containing 0.5 ng/ml $^{125}$I-AB isoform. Labeling was terminated with four rinses of binding medium and cell-associated $^{125}$I-AB isoform determined by extraction with PBS containing 1% Triton X-100. Standard curves were obtained using 0, 0.125, 0.25, 0.5, 1.0, and 2.0 ng/ml purified AB isoform and test samples were compared to these values.

C. Purification of PDGF Isoforms

The monoclonal antibodies 127.5.7.3.1, 120.1.2.1.2 and 121.6.1.1.1 were coupled to CNBr-activated Sepharose (Pharmacia, Piscataway, NJ), under conditions specified by the manufacturer, at a ratio of 10 mg antibody to 1 gram of dry gel. The coupling efficiency was greater than 90% for each antibody. 5 ml of each of the antibody-Sepharose gels was used for the immunoaffinity chromatography.

Figure 9:
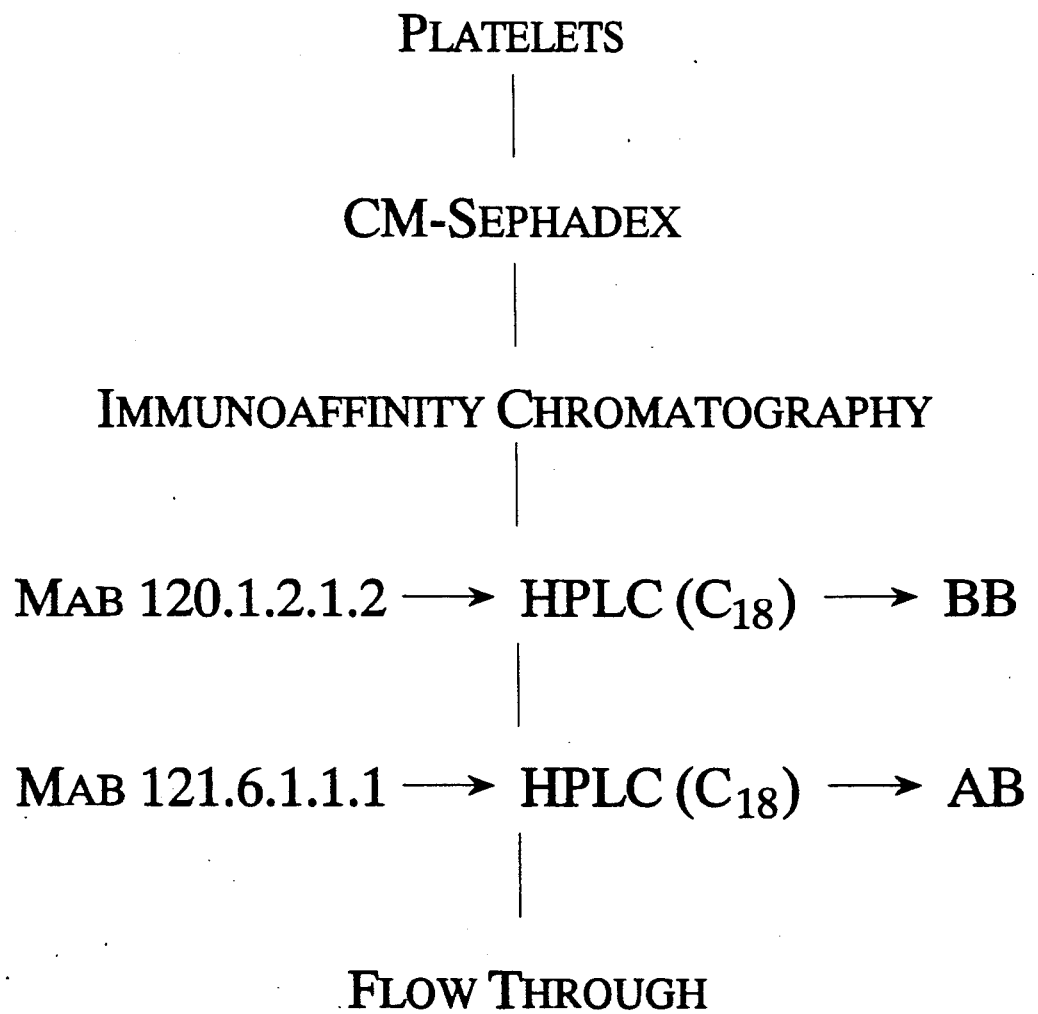
FIG. 9 is a flow diagram of PDGF isoform purification from platelets.

BB and AB isoforms were isolated from platelet lysates using an antibody 120.1.2.1.2 column followed by an antibody 121.6.1.1.1 column. This purification scheme is outlined in FIG. 9. The platelet lysate sample was thawed and any precipitate was removed by centrifugation at $35,000 \times g$ for 60 minutes at 4° C. The sample was then loaded onto the antibody 120.1.2.1.2-Sepharose column This antibody column binds only the BB isoform of PDGF. The sample was cycled over the column for three hours at 4° C. The antibody 121.6.1.1.1-Sepharose column was then added in series with the first column (120.i.2.1.2-Sepharose) and the sample cycled for 12 hours at 4° C. This column binds the AB and BB isoforms of PDGF, but the removal of the BB isoform by the first column (120.1.2.1.2-Sepharose) resulted in the binding of only AB-dimer material on the second column The columns were washed in series with 200 ml of PBS (pH 7.2), 0.5M NaCl. The columns were then eluted separately with 0.1M glycine, pH 2.5. The peak fractions for PDGF activity, determined by radioreceptor assay (as described above), were pooled and chromatographed by HPLC on a Micro Pak SP C18 column (Varian, Palo Alto, CA) using a 0-100% acetylnitrile gradient containing 0.1% trifluoroacetic acid. The peak fractions containing PDGF activity, as determined by radioreceptor assay, were pooled and lyophilized.

AA isoform was purified from conditioned yeast media as follows. An appropriately grown culture of yeast, comprising strain E18 #9 transformed with pA7M, was pelleted to remove the yeast cells and the supernatant was harvested. The supernatant broth was concentrated using Millipore Pellicon Cassettes (Millipore, Bedford, Mass.). The concentrate was neutralized to pH 7.2 with 1M tris-base, pH 8.0. The sample was then centrifuged at $35,000 \times g$ and the supernatant was harvested.

The neutralized concentrate was applied to an antibody 127.5.7.3.1-Sepharose column. The sample was recycled over the column for 12 hours at 4° C. The column was extensively washed with PBS and the AA isoform was eluted from the column with 0.1 M glycine, pH 2.5. The purity of the sample was determined to be greater than 90% by SDS-PAGE and silver staining.

Amino acid composition analysis was done for both the purified platelet BB and AB preparations to determine the protein concentration. Amino acid composition was determined for the purified PDGF isoforms as described in Example IV. By this method, it was determined that the material purified from the antibody 120.1.2.1.2-Sepharose column contained pure BB isoform, as indicated by the lack of detectable tyrosine residues This indicates that no A-chain was present since only the A-chain of PDGF contains tyrosine residues.

The purified BB and AB preparations were also subjected to amino acid sequencing. The N-terminal sequence of the preparations was determined by automated Edman degradation using an applied Biosystems Model 470A gas-phase protein sequencer equipped with a 120A on-line phenylthiohydantoin amino acid analyzer (Applied Biosystems, Foster City, CA).

A-chain and B-chain sequences were obtained in equimolar amounts for the AB isoform isolated by sequential affinity chromatography on monoclonal antibodies 120.1.2.1.2 followed by 121.6.1.1.1. Only B-chain sequence was detected for the BB isoform isolated by affinity chromatography on monoclonal antibody 120.1.2.1.2.

The results for BB and AB isoform purification from platelet lysates are summarized in Table 8. A total of 38 ug of BB isoform and 140 ug of AB isoform were purified as determined by amino acid composition analysis. The total yield of 178 ug provides a 2529-fold purification from the CM-Sephadex eluate. The overall yield for PDGF purification was 73% from the CM-Sephadex eluate.

TABLE 8

| Step | Protein | PDGF Activity[1] |
|---|---|---|
| CM-Sephadex Imunoaffity Columns | 450 mg | 250 ug |
| 120.1.2.1.2 | N.D. | 38 ug |
| 121.6.1.1.1 | N.D. | 144 ug |
| HPLC | | |
| 120.1.2.1.2 | 38 ug[2] | N.D. |
| 121.6.1.1.1 | 140 ug[2] | N.D. |

[1] PDGF activity was determined by radioreceptor assay
[2] Protein concentration was determined by amino acid composition analysis
N.D. - Not determined

EXAMPLE XI

Detection Assay for PDGF Isoforms

The BB isoform of PDGF was detected using an isoform-specific ELISA employing monoclonal antibody 120.1.2.1.2 and a polyclonal rabbit antisera against BB isoform. The wells of a 96-well microtiter plate were coated with a solution containing 2.5 ug/ml antibody 120.1.2.1.2 in ELISA buffer A (Table 4). The plates were incubated with the antibody for two hours at 37° C. Excess antibody was removed by washing the wells with ELISA buffer C (Table 4). The wells were then incubated with ELISA buffer B (Table 4) for two hours at 37° C. to coat the wells and prevent nonspecific binding of the test samples to the wells. The test samples were added to the antibody-coated wells and the plates were incubated for one hour at 37° C. The wells were washed with ELISA buffer C, and rabbit anti-BB isoform sera (diluted 1:500 with ELISA buffer B) was added and the wells were incubated for one hour at 37° C. The wells were then washed with ELISA buffer C. Goat anti-rabbit IgG conjugated to alkaline phosphatase (Sigma, St. Louis, M0) was added and the plates were incubated one hour at 37° C. The wells were washed with ELISA buffer C, then incubated with alkaline phosphatase substrate color reagent (Sigma) diluted into ELISA buffer D. The level of color development was determined by reading the absorbance of the samples at 405 nm. The level of BB isoform in the test samples was determined by comparing the data to a standard curve generated using purified recombinant BB isoform. AB isoform was found to have less than 5% crossover in this assay.

AB isoform was detected using a second assay which also detects the BB isoform. This assay is similar to the BB assay except that antibody 121.6.1.1.1 was used in place of antibody 120.1.2.1.2, and a pool of rabbit anti-BB and rabbit anti-AA antisera were used in place of rabbit anti-BB alone.

Data from representative ELISA assays monitoring antibody crossreactivity are summarized in Table 9. Numbers are absorbance detected at 405 nm using a Dynatech ELISA plate reader.

TABLE 9

| Antibody | Ligand Concentraton (ng/ml) | Ligand BB | AB | AA |
|---|---|---|---|---|
| 120.1.2.1.2 | 32 | .465 | .003 | .001 |
|  | 16 | .318 |  |  |
|  | 8 | .163 |  |  |
|  | 4 | .076 |  |  |
|  | 2 | .021 |  |  |
|  | 1 | .003 |  |  |
|  | 0 | .000 |  |  |
| 121.6.1.1.1 | 50 | .739 | — | .010 |
|  | 32 | — | .783 |  |
|  | 25 | .533 | — |  |
|  | 16 | — | .614 |  |
|  | 12.5 | .309 | — |  |
|  | 8 | — | .528 |  |
|  | 6.25 | .159 | — |  |
|  | 4 | — | .380 |  |
|  | 3.15 | .081 | — |  |
|  | 2 | — | .273 |  |
|  | 1 | — | .172 |  |
|  | 0 | .000 | .000 |  |

I claim:

1. A monoclonal antibody that specifically binds to the PDGF-BB isoform.

2. The monoclonal antibody of claim 1 wherein said antibody is tagged with a label capable of providing a detectable signal.

3. The monoclonal antibody of claim 1 wherein the antibody is of the subclass $IgG_1$.

4. The monoclonal antibody of claim 1 wherein said antibody blocks the binding of an antibody produced by cell line 120.1.2.1.2, assigned ATCC Accession No. HB 9610, to the PDGF-BB isoform.

5. The cell line 120.1.2.1.2, assigned ATCC Accession No. HB 9610.

6. A monoclonal antibody produced by the cell line of claim 5.

7. A monoclonal antibody that specifically binds to the PDGF-AA isoform.

8. The monoclonal antibody of claim 7 wherein the antibody is of the subclass $IgG_{2b}$.

9. The monoclonal antibody of claim 8 wherein said antibody blocks the binding of an antibody produced by cell line 127.8.2.2.2, assigned ATCC Accession No. HB 9611, to the PDGF-AA isoform.

10. The cell line 127.8.2.2.2, assigned ATCC Accession No. HB 9611.

11. A monoclonal antibody produced by the cell line of claim 10.

12. A monoclonal antibody that specifically binds to the PDGF-AB isoform and the PDGF-BB isoform.

13. The monoclonal antibody of claim 12 wherein said antibody is tagged with a label capable of providing a detectable signal.

14. The monoclonal antibody of claim 12 wherein the antibody is of the subclass $IgG_1$.

15. The monoclonal antibody of claim 12 wherein said antibody blocks the binding of an antibody produced by cell line 121.6.1.1.1, assigned ATCC Accession No. HB 9613 to the PDGF-AB isoform or the PDGF-BB isoform.

16. The cell line 121.6.1.1.1, assigned ATCC Accession No. HB 9613.

17. A monoclonal antibody produced by the cell line of claim 16.

18. A monoclonal antibody that specifically binds to the PDGF-AB isoform and the PDGF-AA isoform.

19. The monoclonal antibody of claim 18 tagged with a label capable of providing a detectable signal.

20. The monoclonal antibody of claim 18 wherein the antibody is of the subclass $IgG_1$.

21. The monoclonal antibody of claim 18 wherein said antibody blocks the binding of an antibody produced by cell line 127.5.7.3.1, assigned ATCC Accession No. HB 9612, to the PDGF-AB isoform or the PDGF-AA isoform.

22. The cell line 127.5.7.3.1, assigned ATCC Accession No. 9612.

23. A monoclonal antibody produced by the cell line of claim 22.

24. A method for determining the presence of the PDGF-BB isoform in a biological sample, comprising:
    incubating a monoclonal antibody that is capable of specifically binding to the PDGF-BB isoform with a biological sample; and
    detecting the presence of immune-complexes formed between said monoclonal antibody and said biological sample, and therefrom determining the presence of the PDGF-BB isoform.

25. The method of claim 24 wherein said monoclonal antibody blocks the binding of an antibody produced by cell line 120.1.2.1.2, assigned ATCC Accession No. HB 9610, to the PDGF-BB isoform.

26. The method of claim 24 wherein said monoclonal antibody is produced by the cell line 120.1.2.1.2, assigned ATCC Accession No. HB 9610.

27. The method of claim 24 wherein the monoclonal antibody is labeled.

28. The method of claim 27 wherein said label is selected from the group consisting of radionuclides, fluorophores, enzymes and luminescers.

29. The method of claim 27 wherein the step of detecting is by measurement of radioactivity, fluorescence, enzyme reaction or luminescence emission of said label.

30. The method of claim 24 wherein the biological sample is selected from the group consisting of blood, urine, plasma, serum, platelet and other cell lysates, platelet releasates, cell suspensions, cell-conditioned culture media and chemically or physically separated portions thereof.

31. The method of claim 24 including, after the step of incubating, incubating the monoclonal antibody/sample with a labeled antibody that is capable of binding to the PDGF-BB isoform or the monoclonal antibody.

32. A method for determining the presence of the PDGF-AA isoform in a biological sample, comprising:
    incubating a monoclonal antibody that is capable of specifically binding to the PDGF-AA isoform with a biological sample; and
    detecting the presence of immune-complexes formed between said monoclonal antibody and said biological sample, and therefrom determining the presence of the PDGF-AA isoform.

33. The method of claim 32 wherein said monoclonal antibody blocks the binding of an antibody produced by cell line 127.8.2.2.2, assigned ATCC Accession No. HB 9611, to PDGF.

34. The method of claim 32 wherein said monoclonal antibody is produced by the cell line 127.8.2.2.2, assigned ATCC Accession No. HB 9611.

35. The method of claim 32 wherein the monoclonal antibody is labeled.

36. The method of claim 35 wherein said label is selected from the group consisting of radionuclides, fluorophores, enzymes and luminescers.

37. The method of claim 35 wherein the step of detecting is by measurement of radioactivity fluorescence, enzyme reaction or luminescence emission of said label.

38. The method of claim 32 wherein the biological sample is selected from the group consisting of blood, urine, plasma, serum, platelet and other cell lysates, platelet releasates, cell suspensions, cell-conditioned culture media and chemically or physically separated portions thereof.

39. The method of claim 32 including, after the step of incubating, incubating the monoclonal antibody/sample with a second labeled antibody that is capable of binding to the PDGF-AA isoform or the monoclonal antibody.

40. A method for purifying native PDGF from a sample, comprising:
    immobilizing monoclonal antibodies, capable of specifically binding to native PDGF, selected from the group consisting of antibodies that block the binding of an antibody produced by cell line 120.1.2.1.2 (ATCC Accession No. HB 9610) to the PDGF-BB isoform, antibodies that block the binding of an antibody produced by cell line 127.8.2.2.2 (ATCC Accession No. HB 9611) to the PDGF-AA isoform, antibodies that block the binding of an antibody produced by cell line 121.6.1.1.1 (ATCC Accession No. HB 9613) to the PDGF AB isoform or the PDGF-BB isoform, and antibodies that block the binding of an antibody produced by cell line 127.5.7.3.1 (ATCC Accession No. HB 9612) to the PDGF-AB isoform or the PDGF-AA isoform, on a substrate;
    contacting the sample containing native PDGF with the immobilized monoclonal antibodies under suitable conditions such that the native PDGF binds to said antibodies; and
    eluting the native PDGF from the monoclonal antibodies.

41. The method of claim 40 wherein the substrate is selected from the group consisting of polymeric tubes, beads, polysaccharide particulates, and polyacrylamide.

42. The method of claim 40 wherein the sample is selected from the group consisting of blood, urine, plasma, serum, platelet and other cell lysates, platelet releasates, cell suspensions, cell-conditioned culture media and chemically or physically separated portions thereof.

43. The method of claim 40 including, after the step of contacting, separating unbound sample from the immobilized monoclonal antibodies.

44. A method for purifying the PDGF-BB isoform from a sample, comprising:
    immobilizing monoclonal antibodies, capable of specifically binding to the PDGF-BB isoform, on a substrate;
    contacting the sample containing native PDGF with the immobilized monoclonal antibodies under suitable conditions such that the PDGF-BB isoform binds to said antibodies; and
    eluting the PDGF-BB isoform from the monoclonal antibodies.

45. The method of claim 44 including, after the step of contacting, separating unbound sample from the immobilized monoclonal antibodies.

46. A method for purifying the PDGF-AA isoform from a sample, comprising:
    immobilizing monoclonal antibodies, capable of specifically binding to the PDGF-AA isoform, on a substrate;
    contacting the sample containing the PDGF-AA isoform with the immobilized monoclonal antibodies under suitable conditions such that the PDGF-AA isoform binds to said antibodies; and
    eluting the PDGF-AA isoform from the monoclonal antibodies.

47. The method of claim 46 including, after the step of contacting, separating unbound sample from the immobilized monoclonal antibodies.

48. A diagnostic kit for assaying the presence of native PDGF, comprising, in a suitable package;
    a monoclonal antibody, capable of binding to native PDGF, selected from the group consisting of an antibody that blocks the binding of an antibody produced by cell line 120.1.2.1.2 (ATCC Accession No. HB 9610) to the PDGF-BB isoform, an antibody that blocks the binding of an antibody produced by cell line 127.8.2.2.2 (ATCC Accession No. HB 9611) to the PDGF-AA isoform, an antibody that blocks the binding of an antibody produced by cell line 121.6.1.1.1 (ATCC Accession No. HB 9613) to the PDGF AB isoform or the PDGF-BB isoform, and an antibody that blocks the binding of an antibody produced by cell line 127.5.7.3.1 (ATCC Accession No. HB 9612) to the PDGF-AB isoform or the PDGF-AA isoform, and a labeled polyclonal antibody that is capable of binding to native PDGF wherein the monoclonal antibody and the polyclonal antibody are contained within the same or separate containers within said package.

49. A diagnostic kit for assaying the presence of the PDGF-BB isoform, comprising, in a suitable package:
a monoclonal antibody capable of specifically binding to the PDGF-BB isoform, and a labeled polyclonal antibody that is capable of binding to the PDGF-BB isoform wherein the monoclonal antibody and the polyclonal antibody are contained within the same or separate containers within said package.

50. A diagnostic kit for assaying the presence of the PDGF-AA isoform, comprising, in a suitable package:
a monoclonal antibody capable of specifically binding to the PDGF-AA isoform, and a labeled polyclonal antibody that is capable of binding to the PDGF-AA isoform wherein the monoclonal antibody and the polyclonal antibody are contained within the same or separate containers within said package.

* * * * *